(12) United States Patent
Zweig

(10) Patent No.: US 7,288,368 B2
(45) Date of Patent: Oct. 30, 2007

(54) MEMBRANE RECEPTOR REAGENT AND ASSAY

(76) Inventor: Stephen Eliot Zweig, 224 Vista de Sierra, Los Gatos, CA (US) 95030

( * ) Notice: Subject to any disclaimer, the term of this patent is extended or adjusted under 35 U.S.C. 154(b) by 441 days.

(21) Appl. No.: 10/885,429

(22) Filed: Jul. 6, 2004

(65) Prior Publication Data

US 2004/0241765 A1 Dec. 2, 2004

Related U.S. Application Data

(63) Continuation-in-part of application No. 10/444,390, filed on May 23, 2003, now Pat. No. 6,790,632.

(60) Provisional application No. 60/428,137, filed on Nov. 21, 2002, provisional application No. 60/400,396, filed on Jul. 31, 2002, provisional application No. 60/389,679, filed on Jun. 17, 2002.

(51) Int. Cl.
*C12Q 1/00* (2006.01)
(52) U.S. Cl. .................... 435/4; 436/518; 436/519; 436/535; 435/7.92; 435/968
(58) Field of Classification Search ............ 435/4, 435/7.1, 7.21, 7.92, 968; 436/165, 172, 518, 436/829, 519, 535; 422/82.11
See application file for complete search history.

(56) References Cited

U.S. PATENT DOCUMENTS

| | | |
|---|---|---|
| 5,434,084 A | 7/1995 | Burgess, Jr. |
| 5,494,803 A | 2/1996 | Carbonell et al. |
| 5,512,492 A | 4/1996 | Herron et al. |
| 5,641,640 A | 6/1997 | Hanning |
| 5,837,196 A | 11/1998 | Pinkel |
| 5,922,594 A | 7/1999 | Lof.ang.s |
| 5,965,456 A | 10/1999 | Malmqvist et al. |
| 6,228,326 B1 | 5/2001 | Boxer et al. |
| 6,274,872 B1 | 8/2001 | Katerkamp |
| 6,289,296 B1 | 9/2001 | Umeno |

(Continued)

OTHER PUBLICATIONS

Schena, "Microarray Biochip Technology", 2000, Eaton Publishing, Natick MA.

(Continued)

*Primary Examiner*—Long V. Le
*Assistant Examiner*—Nelson Yang

(57) ABSTRACT

A membrane receptor reagent and assay is disclosed in which liposomes are bound to an evanescent wave emitting surface. Membrane receptors on the liposome's fluid lipid bilayer membrane are labeled with a fluorescent or luminescent moiety. These membrane receptors are free to diffuse randomly throughout the liposome surface, and thus tend to redistribute according to externally applied forces. The evanescent wave-emitting surface additionally contains reagents that reversibly bind to the membrane receptors, tending to bring them closer to region of high evanescent wave intensity. Test analytes that disrupt or promote the association between the membrane receptors and the surface reagents act to change the average distance between the membrane receptors and the evanescent wave emitting surface, resulting in a change in the fluorescent or luminescent signal. This reagent and assay system functions with physiologically important membrane receptors such as GPCR receptors, other 7-tm receptors, drug transport proteins, cytochrome P450 membrane proteins and other clinically important membrane components. The reagent and assay methods may be incorporated into microarrays, capillaries, flow cells and other devices, and used for drug discovery, ADMET, and other biomedically important assays.

20 Claims, 11 Drawing Sheets

U.S. PATENT DOCUMENTS

| | | |
|---|---|---|
| 6,316,274 B1 | 11/2001 | Herron et al. |
| 6,395,558 B1 | 5/2002 | Duveneck et al. |
| 6,493,097 B1 | 12/2002 | Ivarsson |
| 2002/0019015 A1 | 2/2002 | Lahin et al. |
| 2002/0094544 A1 | 7/2002 | Fang et al. |

OTHER PUBLICATIONS

Mitchell "A perspective on protein microarrays", Nature Biotechnology (20) 2002, 225-229.

Groves et. al. "Micropatterning fluid lipid bilayers on solid supports", Science (275) 1997, 651-653.

Groves, Boxer "Micropattern formation in supported lipid membranes" Acc Chem Res 35(3) 2002, 14.

MacBeath, Schreiber "Printing proteins as microarrays . . . " Science (289), 2000, 1760-1763.

Salafsky et. al. "Architecture and function of membrane . . . " Biochemistry (35) 1996, 14773-14781.

Williams et. al. "Advances in lipid mobilization—The L1 Chip". BIAjournal (7) 2000, 1.

Fang et. al. "Membrane protein microarrays" J. Am Chem Soc 20; 124(11) 2002, 2394-5.

Jung et. al, "Qualification of tight binding to surface-immobilized phospholipid vesicles . . . " 2000 J. Am. Chem. Soc., 122, 4177-4184.

Wagner et. al, "Tethered Polymer Supported Planar Lipid Bilayers . . . " Biophys J, 2000, 79, p. 1400-1414.

MEMBRANE RECEPTOR REAGENT AND ASSAY

This patent is a continuation in part of patent application Ser. No. 10/444,390 "Membrane receptor reagent and assay", filed May 23, 2003 now U.S. Pat. No. 6,790,632. Application Ser. No. 10/444,390 claimed priority benefit of provisional patent applications 60/389,679; and 60/400,396 both entitled "Tethered receptor-ligand reagent and assay", filed Jun. 17, 2002 and Jul. 31, 2002; and provisional patent application 60/428,137; entitled "Membrane receptor reagent and assay", filed Nov. 21, 2002.

BACKGROUND OF THE INVENTION

1. Field of the Invention

The invention generally concerns reagents and methods useful for membrane receptor-ligand binding assays.

2. Description of the Related Art

Much of modern pharmacology and biochemistry is focused on the interactions between different types of biological signaling molecules and their corresponding membrane receptors. Structurally, these membrane receptors are often G-Protein Coupled Receptors (GPCR) from the 7-transmembrane (7tm) protein family, and other types of related 7-transmembrane proteins such as ion channels.

Biological signaling molecules and membrane receptors are present in many physiological processes, and are particularly important for nervous system function. Indeed, nervous system membrane receptor systems, such as the dopamine, serotonin, and opioid receptor families, have been found to be involved in many mental disorders, such as anxiety, depression, and drug abuse. Furthermore, these membrane receptors have been found to be excellent drug targets. GPCR reactive drugs are involved in many other biological processes as well. *Kenakin, Annu Rev Pharmacol Toxicol* 2002;42:349–79).

To date, however, only a small number of the many possible interactions between the millions of potential candidate drug ligands, and the thousands of different membrane receptors, have been well characterized. With the recent advances in both genomics and nucleic acid microarray technology, the cellular distribution and sequence of these membrane receptors and receptor families are now readily available. As a result, one of the key challenges going forward is to utilize this new knowledge to aid in the development of next generation drugs.

Modern drug discovery and development is a multi-step process. Usually, one or more medically important target receptors are identified, a large number of prototype lead drugs are synthesized, and appropriate High Throughput Screening (HTS) assays are conducted to assess the proper differential binding to an initial set of selected target and non-target receptors. Those lead candidates that survive the process are then subjected to progressively more expensive and stringent assays; whole cell assays, animal studies, Absorption, Distribution, Metabolism, Excretion, Toxicity (ADMET) studies, and finally human Phase I, II, and III studies. The expense and time involved in the later stages, typically hundreds of millions of dollars and many years, are such that it is enormously important that optimal leads be found as early in the process as possible.

One of the best ways to exploit the recent advances in genomics is to use the information to clone and express these membrane receptors in a pure state, and use these cloned receptors for HTS lead identification and optimization. In theory, the later stages of drug development could be significantly streamlined if low-cost and efficient HTS methods were developed to initially optimize a lead's specific binding to its target receptor, and to detect any unwanted cross-reaction with non-target receptors.

At present, however, membrane HTS screening methods are sub-optimal. Membrane proteins are hydrophobic, and typically only assume their correct physiological conformation in a lipid bilayer membrane environment. Moreover, many membrane receptor proteins rely upon certain aspects of lipid bilayers, such as receptor lateral mobility, association with lipid rafts, association with other proteins, small molecule cofactors etc., for proper function. Such faithful recreations of native membrane structures are difficult to reproduce in a synthetic, in-vitro, environment.

As a result, present membrane HTS screening methods usually rely upon the binding of radioactively labeled ligands to natural membrane receptors (e.g. receptors obtained from natural sources such as cultured cells). These natural membrane receptors are often bound to a solid phase, such as a filter or microwell plate. Radioactive ligand is applied to the sample, followed by one or more washing steps. The bound radioactive ligand is then detected by its radioactive scintillation signal. Thus relatively large quantities of membrane proteins and candidate drug ligands are required for each assay. For example, even the optimized Packard Bioscience FlashPlate™ system requires 25 to 50 ul of fluid for each assay point.

Although the use of natural membranes has strong physiological merit, it is slow, expensive, and cumbersome. An alternate membrane receptor HTS methodology that could return physiologically useful data with cloned membrane receptors would be highly advantageous, as it would enable the many recent genomic insights to be easily and rapidly used.

An ideal membrane-receptor HTS methodology would have a number of other characteristics as well. At present, HTS methods are typically restricted to large, well-financed, commercial organizations. This is because the present methodologies require the use of large quantities of expensive membrane receptors, expensive synthetic drug candidates, and expensive automation. If alternative methods could be devised to reduce the quantities of receptors and synthetic drug candidates by several orders of magnitude, the financial and logistical burden of HTS studies would be greatly eased. This would enable a much larger number of receptors and drug candidates to be screened, and could also make HTS methods feasible in smaller scale settings, such as academic laboratories. One good way to accomplish this goal is by the development of suitable membrane receptor microarray technology.

Microarray technology: In recent years, microarrays have become widely used for genomic and proteomic biotechnology, biomedical research, and biomedical diagnosis. In particular, microarray methods have become widely used for nucleic acid research, and a large number of nucleic acid microarrays are commercially available from Affymetrix Inc., Incyte Pharmaceuticals, Inc., and many other companies. These methods (reviewed in *Schena, Microarray Biochip Technology* (2000) Eaton Publishing, Natick, Mass.) generally work by binding a large number of nucleic acid microsamples to the surface of a flat support. Samples containing one or more unknown complementary nucleic acids are then exposed to the nucleic acid microarray, and the sample is allowed to hybridize to the microarray. Hybridized nucleic acids are then detected by various means, and the overall nucleic acid composition of the unknown sample is assessed.

The general principle has been that to detect two biologically interacting elements that form a pair, such as complementary nucleic acid strands, the microarray will contain one-half of the pair, the unknown analyte will contain the other half of the pair, and the interaction between the two elements will generate a detectable signal.

A good overview of protein microarray technology in general, as it exists at the time of this patent application, can be found in the article by Mitchell, "*A perspective on protein microarrays*", *Nature biotechnology* (20), 2002, 225–229, the contents of which are incorporated herein by reference.

There have been some previous attempts to produce membrane receptor microarrays, such as U.S. Pat. No. 6,228,326; and Salafsky et. al., *Biochemistry* (1996) 35: 14773–14781. One approach, pioneered by Boxer and coworkers (Groves et. al., *Science* (1997), 275: 651–653) relies upon the formation of an artificial planar lipid membrane parallel to a microarray surface. The microarray uses a series of mechanical barriers to separate one lipid region from another, enabling multiple regions to be patterned. The microarray is analyzed by fluorescence recovery after photobleaching (FRAP) techniques. Here, fluorescent membrane components are exposed to a localized region of intense laser irradiation. Following irradiation, a bleached region forms, which can be observed by a fluorescence microscope. This gradually disappears as unbleached membrane components from surrounding regions gradually migrate into the bleached region.

Although useful for demonstration purposes, one fundamental critique of this approach is that due to the close (1 nm) association between the inner leaflet of the artificial membrane lipid bilayer, and the solid phase support, the physiology of the artificial membrane is highly distorted. In particular, larger membrane proteins, such as GPCR proteins, are large enough that they can interact with the solid phase support, resulting in distorted conformations and inactivity. Additionally, the narrow aqueous layer is too thin to enable GPCR proteins to interact with other cytoplasmic side cofactors, which play a key role in the proper function of the receptor.

A second critique of this approach is that FRAP detection techniques are too crude to spot many interesting types of interactions. For example, these methods are of marginal utility for drug discovery purposes. This is because the binding of the relatively small (low molecular weight) drug candidates to relatively large (high molecular weight) membrane receptors will have a negligible impact on the FRAP mobility of the receptors, and thus will be poorly detected by FRAP techniques.

An alternative type of membrane microarray has been proposed by Ziauddin and Sabatini that relies on DNA uptake (Ziauddin J, Sabatini D M, "*Microarrays of cells expressing defined cDNAs*", Nature, 2001, 411:107–10). Here, DNA coding for receptor genes is spotted on a microarray surface. After spotting, cells are cultured on the microarray. Those cells located above the DNA spots take up the DNA, and express the appropriate receptor on the cell surface. This is a relatively new approach, and more work will be needed before the relative utility of such microarrays can be accurately assessed.

The "L1" chip produced by Biacore Corporation represents a third technique (Williams, C., Cook S., Knoppers M., "*Advances in Lipid Immobilization: The L1 Chip*", BIAjournal 2000, 7 (1)). In this technique, membrane fragments from mammalian cells are bound to the surface of a flowcell. Samples containing potential ligands are injected into the flow cell, and after a washing step, retained material is eluted and analyzed by mass spectroscopy.

Although this technique is clearly useful for certain analytical needs, it has some drawbacks. The present L1 chip design has hydrophobic moieties on the surface of the chip. These interact with membrane samples, causing liposomes and membrane vesicles to rupture. As a result, the applied membranes become firmly attached to the surface of the chip with no aqueous separation layer (Erb E, Chen X, Allen S, Roberts C, Tendler S, Davies M, Forsen S. "*Characterization of the surfaces generated by liposome binding to the modified dextran matrix of a surface plasmon resonance sensor chip*" Anal Biochem 2000, 280(1):29–35). Thus, as is the case for the Boxer design, ligand-binding reactions are distorted. Additional drawbacks are the relatively slow throughput of the single element flow-cell design, and a large number of false positives produced by the mass-spectrometer detection methodology.

Evanescent wave technology: Evanescent waves are generated when a light wave undergoes total internal reflection at a surface (a junction between two media with different indexes of refraction). A light wave travels through the first media until it encounters the surface boundary, and, at the appropriate angle of incidence (the critical angle), bounces back from the surface and continues traveling through the first media, rather than entering into the second media. Here, a small amount of energy, termed an evanescent wave, penetrates an extremely short distance into the second media, and rapidly decays in intensity as distance from the boundary increases. For optical frequencies and media types commonly used in biological research, the evanescent wave decreases in intensity by about 1/e (that is, about $\frac{1}{2.71}$) over a distance of about 260 nm. Thus, over distances of a few hundred nanometers, evanescent wave excitation is a good way to determine the relative distance between an excitable moiety, and a surface boundary.

Evanescence biosensor techniques are known in the art, but have not been generally used for membrane bound analytes. For example, U.S. Pat. No. 6,316,274 teaches multi-analyte biosensor methods using fluorescence moieties excited by evanescence illumination. Other representative prior art includes U.S. Pat. Nos. 6,274,872; 5,512,492; and 6,395,558.

Lipid membrane and liposome technology: As first described by Singer and Nicolson (*Science* 1972 Feb. 18; 175(23):720–31), biological membranes are composed of a hydrophobic lipid bilayer, with membrane proteins existing as compact "ice berg" like structures floating embedded in this lipid bilayer, which is about 6 nm thick. Due to the weak nature of hydrophobic bonds, lipids and integral membrane proteins are able to move freely (lateral mobility) within the plane of the lipid membrane. In particular, when exposed to forces from external ligands, such as bivalent antibodies, lectins, etc., membrane proteins and other lipid components are able to diffuse together to form "patches" or "caps" on the membrane surface.

Because biological lipid membranes are highly complex structures with many different types of membrane proteins, biochemists and molecular biologists typically find it preferable to work with simplified synthetic lipid membranes, reconstituted from purified components. Such synthetic membranes can be synthesized by simple methods, since they tend to spontaneously form when lipid mixtures (which may also contain membrane proteins) are dissolved in detergents, and the detergent then gradually removed by dialysis or other process. The resulting synthetic membrane structure typically forms as a "soap-bubble-like" structure called a "liposome" or "phospholipid vesicle". The walls of the liposome consist of lipid bilayers, and the membrane proteins typically insert themselves into the artificial lipid bilayer with the correct, or nearly correct, conformation. Depending upon the synthetic process, liposomes can be formed with diameters ranging from about 50 nm to 5,000+ nm.

Artificial liposomes (phospholipid vesicles) containing lipids and protein can be created by a number of methods, including cadmium synthesis (*Thromb Haemost* 1980 Aug. 29; 44(1): 12–5); dialysis against octyl glucoside (*Biochemistry* 1986 Jul. 15; 25(14): 4007–20); deoxycholate (*Biochem J* 1977 Jul. 1; 165(1): 89–96), and numerous other methods.

Membrane proteins: Many biologically relevant proteins are transmembrane proteins. These proteins exist embedded in membrane lipid bilayers, and typically can best be studied while associated with intact membranes. These transmembrane proteins include the 7-transmembrane proteins (reviewed by Kilpatrick et. al. *J Cell Sci* 2001 February;114(Pt 4):629–41), and their medically relevant subfamily, the G-protein cell receptors (GPCR family), (reviewed by Woodside, *Sci STKE* 2002 Mar. 19;2002(124):PE14). Other relevant transmembrane proteins include the integrin family, the cadherin family (reviewed by Angst, et. al, *J Cell Sci* 2001 February;114(Pt 4):629–41), and many others.

ADMET assays: The current art in in-vitro ADMET assays is described by Darvas and Dorman in *High-Throughput ADMETox Estimation: In Vitro & In Silico Approaches*, (2002) BioTechniques Press, Eaton Publishing, Westborough, Mass.

An ideal membrane receptor microarray would be both physiologically realistic and biochemically well defined. To do this, an ideal microarray should present membrane targets in an environment that, from both sides of the lipid bilayer, enables receptor binding proteins and other cofactors to interact in a normal manner. Additionally, an ideal membrane microarray should be able to detect the binding reactions between large numbers of different low molecular weight drug candidate ligands, and different membrane receptors. Finally, an ideal membrane receptor microarray should function using ultra-small quantities of candidate drug ligands, and ideally also be reusable.

SUMMARY OF THE INVENTION

Here, a novel type of membrane-receptor reagent, suitable for high performance membrane receptor microarrays, is taught. As will be discussed in later sections, this type of microarray may have high utility for HTS drug discovery and development. For example, a comprehensive GPCR microarray, containing a large number of different GPCR families and common GPCR variants, would detect unwanted cross-reactions at the earliest stage of the drug discovery process. This would greatly facilitate the development of highly specific and well-targeted new drugs.

The invention consists of a reagent system for monitoring the interaction between one or more membrane receptors of interest (here designated as "target membrane receptors"), and one or more experimental ligands. These experimental ligands may be drugs, drug candidates, receptor agonists, antagonists, inhibitors, ect., and are here designated as "test ligands" This reagent system consists of:

(1) A fluid lipid membrane containing a target membrane receptor molecule labeled with a moiety that produces a detectable signal upon receiving excitation energy, and in which the fluid lipid membrane acts as a flexible tether for the receptor.

(2) A "reagent ligand" tethered to a surface that emits energy capable of exciting the receptor's detectible signal emitting moiety. This excitation energy diminishes sharply in intensity as distance from the surface increases. This reagent ligand binds to the target membrane receptor molecule in a reversible manner. This reagent ligand is always present in the reagent portion of the system, and it's binding to the target membrane receptors may, or may not, be disrupted depending upon the presence and properties of the unknown "test ligand".

(3) Anchor linking means that bind the lipid membrane and the surface into a single linked structure. This structure utilizes the fluid nature of the lipid membrane to allow the target membrane receptors to associate and dissociate from their binding site on the reagent ligands. The geometry and the tethering action of the fluid lipid membrane is such that if the bond between the target membrane receptor and the reagent ligand is disrupted, the target membrane receptor is free to diffuse far enough away from the energy emitting surface so as to produce a significant change in the amount of excitation energy received by the moiety associated with the target membrane receptor.

Typically, the lipid membrane is in the form of a liposome. In use, the reagent system is typically exposed to one or more test ligands. These test ligands may either enhance or disrupt the association between the target membrane receptor and the surface bound reagent ligand. The ability of the test ligand to modulate this association is thus monitored by observing changes in the detectable signal emitted by the moiety labeled target membrane receptor.

Usually, the liposome-associated target membrane receptor molecule will be a transmembrane protein that is of biological interest, such as the 7-transmembrane proteins (particularly "GPCR" proteins), toll-like receptors, transport proteins, biological response modifier receptor proteins, coagulation factors, immune response receptors, enzymes, and other biologically interesting cellular receptors.

The reagent ligand that is tethered to the surface may be any molecular entity that binds to the liposome-associated target membrane receptor molecule. Usually, the target membrane receptor will be a receptor for biological signaling molecules, such as a GPCR receptor. In this case, the bound reagent ligand will often be the natural target, an agonist, or a synthetic analog of the biological signaling molecules that are bound by the target membrane receptor.

Alternative binding reactions are also possible, however. For example, the liposome bound target membrane receptor may be an enzyme. In this case, the reagent ligand may be a substrate or inhibitor of the enzyme. Alternatively, the liposome bound target membrane receptor may itself be an enzyme substrate. In this case, the reagent ligand may be an enzyme, or a molecule with similar binding properties as the natural enzyme that reacts with the target membrane receptor.

As yet another alternative, the liposome bound target membrane receptor may be an antigen, and the reagent ligand may be an antibody that binds to the antigen.

As a third alternative, the target membrane receptor may be a transport protein, such as an ABC drug transporter protein, and the reagent ligand may be a ligand or analog to a ligand that is normally transported by the transport protein.

As previously discussed, the target membrane receptor will usually be labeled with a moiety that is capable of emitting a detectable signal when exposed to an outside energy source. The lipid membrane in turn will be tethered to an energy-emitting surface, where the energy emitted by the surface changes sharply as a function of distance away from the surface. Also tethered to this surface (by different means) will be a reagent ligand that binds to the target membrane receptor. Due to the fluid nature of the lipid membrane, the resulting target membrane receptor and surface-bound reagent ligand are free to associate and dissociate. Yet both remain attached to the energy-emitting surface.

The geometry of the membrane, and the energy-emitting surface, are chosen so that the detectable signal-emitting moiety on the target membrane receptor is exposed to differing levels of excitation energy depending upon the binding or non-binding of the target membrane receptor to the surface-bound reagent ligand.

A number of different geometric configurations and detection schemes are feasible for these purposes. One particularly favored embodiment is the use of lipid membranes arranged in a spherical liposomal configuration. These spherical liposomes may be tethered to an optical surface that exposes the liposomes to evanescent wave excitation. Here, there will be a gradient in excitation energy between the surface side of the liposome, and the distal side of the liposome. The distribution of target membrane receptors on the liposome surface can thus be assessed by the relative intensity of the signal generated by the detectible signal emitting moieties that are bound to the target membrane receptors.

Other membrane configurations, e.g. lipid layers mounted on a second surface that projects away from an energy emitting surface, and/or other excitation sources (e.g. electrochemiluminescence, chemical gradients, electron transport, resonance energy transfer, etc.), where there is a sharp decrease or increase in energy transfer as a function of distance from the surface, may also be used.

This reagent and method exhibits a number of distinct advantages over the prior art. One distinct advantage is that all of the chemistry required to perform the desired analysis is present on the support as a single homogeneous unit. Thus for each test, no additional chemistry or processing steps (such as washing or centrifugation) are required. Because the reagent contains all necessary detection means, the test-ligands do not need to be artificially labeled in any way. The assay chemistry is inherently reusable, and, by simply applying a wash step between assays, may be reused for multiple assays with different test-ligands. The reagent and method uses several orders of magnitude less reagents than previous art. Since the reagents used in this type of test are typically quite expensive, the economic savings are considerable.

This support may contain a small or large number of different target membrane receptors arranged on different sections of the support. In the case where only a small number of different types of target membrane receptors are present, liposomes containing the target membrane receptors may be applied to the support by simple dipping, coating, spraying, or other means. Alternatively, large numbers of different target membrane receptors may be used, and the support may be a microarray or flow cell that has hundreds or thousands of different target membrane receptors. In this situation, the liposomes may be applied by common microarray sample spotting methods, such as slotted pens, jet printing, and the like. In other situations, the support may be the inside of a capillary tube, or the surface of an optical fiber, in which case more specialized fabrication methods may be required.

For evanescent detection methods, the support containing the energy-emitting surface will normally be made of a solid material, such as glass or plastic, that has an index of refraction that is significantly different from the liposome containing aqueous media. However use of non-solid supports is also possible. As an example, high index of refraction, water and oxygen permeable, porous polymers, such as the materials used for soft contact lenses, may also be suitable.

In some cases, use of composite supports may be desirable. Such composite supports may be composed of a first solid glass or plastic energy emitting support layer that has an index of refraction that is significantly different from the assay's aqueous media, covered with a thin coating of a second material, such as a water permeable porous polymer, which may have an index of refraction substantially similar to the aqueous media. In this case, the underlying glass or plastic support layer may emit evanescent energy, while other test reagents in turn may be coupled to a second layer coated on top of the energy emitting first layer. Such multilayer composites may be used to generate non-flat surfaces where a single lipid bilayer may exist at a variable distance away from an energy-emitting surface.

The liposome reagents will typically need to be anchored to the surface by means that are unaffected by the presence or absence of test-ligands. Additionally, the target membrane receptors on the liposome will themselves usually be tethered to the surface by reversible linkages to surface bound reagent ligands.

Although in some cases, it may be preferable, for each different liposome preparation, to perform this set of linkages by separate set chemical coupling reactions, this approach quickly becomes impractical for systems with a large number of different target membrane receptors. As a result, it is often preferable to employ an "active" support surface with a number of the "generic" components of the tethered receptor-ligand reagent (for example some of the tethering and/or binding components) pre-prepared on the support surface. With an active support, a user may create the final microarray by simply spotting the various liposome preparations onto the active surface. The spotted liposome reagents can then form the appropriate anchoring and reversible reagent ligand linkages with minimal additional effort.

DETAILED DESCRIPTION OF THE INVENTION

Figure 1:
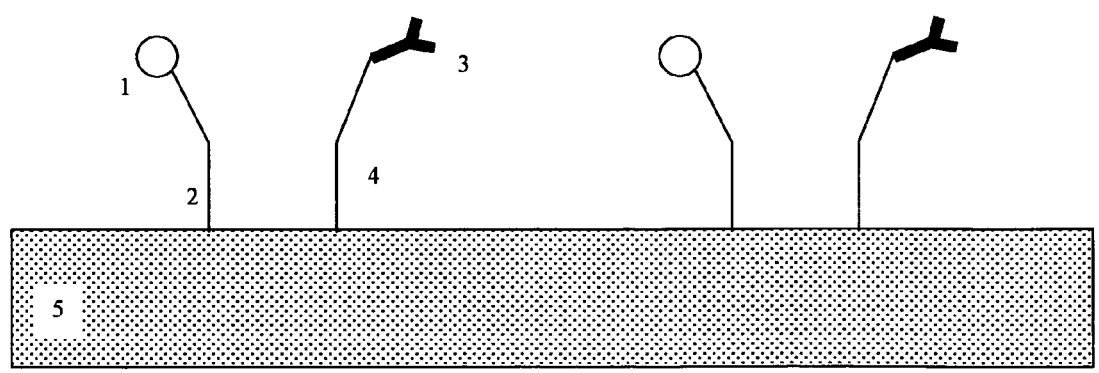
FIG. 1 shows a diagram of a general-purpose microarray active surface, and its interactions with a liposome reagent.
Figure 1:
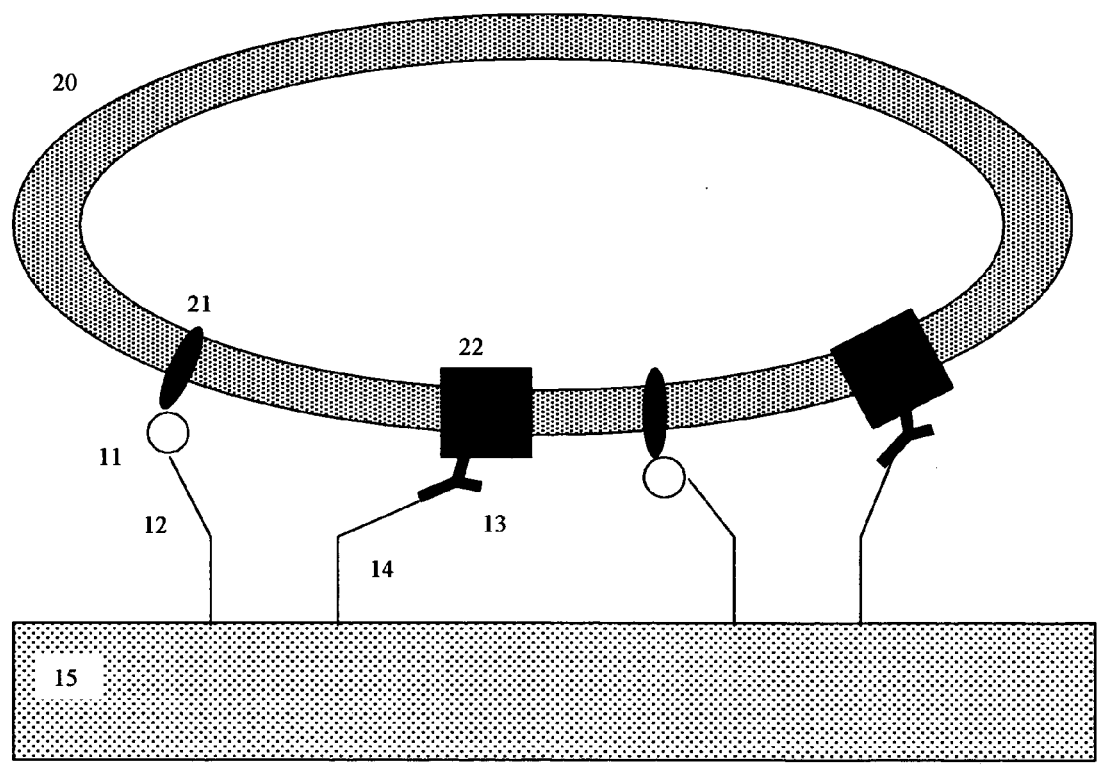

Detection Methods:

Due to the relative scale of the distances involved, detection schemes that are sensitive to positional changes over a liposomal diameter range (50–5000 nm) are needed. For this purpose, techniques such as evanescent wave optics, electrochemiluminescence, electron transport, surface plasmon resonance, and other short-range positional detection modalities are appropriate. Here, evanescent wave optical detection techniques will be explored in more detail.

As previously discussed, evanescent wave detection schemes function over several hundred nanometers. For the purposes of this invention, the essential factor is that the membrane component under investigation must be free to laterally diffuse in a direction roughly perpendicular (towards or away) from an evanescent wave source, or other sharp gradient energy source.

One good way to achieve this end is to incorporate the membrane component into a lipid vesicle such as a liposome, and link the liposome to a surface that emits evanescent waves. Membrane components on the side of the liposome that is closer to the evanescent wave-emitting surface will receive more excitation energy, while membrane components on the side of the liposome that is further away from the evanescent wave-emitting surface will receive less excitation. Thus the relative position of the membrane components may be detected, yet the membrane components remain tethered to the liposome, and the evanescent wave emitting surface, throughout the assay.

Synthetic Liposome and Membrane Synthesis

Synthetic liposomes (or phospholipid vesicles) are usually created by dialysis of the detergent dissolved target membrane receptors, and appropriate lipids, versus a non-detergent containing aqueous solution, using methods such as those of Bach, et. al. (*Biochemistry* 1986 Jul. 15;25(14): 4007–20). This can lead to the spontaneous formation of liposomes with the target membrane receptors embedded into the liposome's lipid bilayer membrane.

The hydrocarbon chain length of the lipids should be long enough to enable a stable membrane structure to form in aqueous solutions, and short enough so that lipids and integral membrane proteins components remain substantially mobile for at least one of the assay temperatures. Often these are lipid mixtures that may include phosphatidylserine, phosphatidylcholine, and/or phosphatidylethanolime. A number of these considerations have been previously taught by Tans et. al., (*Eur J. Biochem*. 95: 449–457, 1979).

In order to obtain useful information, the distribution of the target membrane receptors must be detected by some means. To do this, the target membrane receptors are labeled with a reporter group, which will typically be a fluorescent or luminescent group. In the case of a transmembrane protein, for example, this reporter group may be a carboxy-terminal bound moiety. Alternatively, the target membrane receptors may be genetically engineered to additionally contain a fluorescent or luminescent region, such as a green fluorescent protein or aquelorin region. As a third alternative, a protein or factor that normally binds to the target membrane receptors may itself be fluorescently or luminescently labeled, and the target membrane receptors detected indirectly. This protein or factor does not need to be irreversibly bound to the target membrane receptor for all target membrane receptor conformational states. In some cases, it may be desirable to use a label protein or factor that binds to the target membrane receptor preferentially when the receptor is in one type of conformational state, but not in a different type of conformational state.

For GPCR target membrane receptors, this can be done by incorporating a second fluorescently labeled GPCR binding protein, such as β-arrestin into the liposome. (Labeled β-arrestin is available from Norak Sciences Corporation, Morrisville, N.C.). This can be done by incorporating the GPCR binding protein into the lipid dialysis mix at the time of original liposome synthesis, followed by subsequent washing steps to remove any leftover material adhering to the outside of the liposome.

To irreversibly affix the liposomes to an energy-emitting surface, a separate set of anchor groups is usually required. A number of methods may be used here, such as biotin-avidin or biotin-strepavidin binding techniques. One way to do this is by biotin labeling a membrane component, and using it to "anchor" the membrane component to an avidin group coupled to the surface. This anchor molecule may be a membrane lipid, or an alternate membrane protein that is tightly bound to the membrane, but otherwise does not interact with the liposome's target membrane receptors. This liposome "anchor" molecule simply functions to hold the liposome in position, and is otherwise not active in the assay. Ideally, the liposome anchors will not otherwise interact with the target membrane receptors on the liposomes, nor with the test ligands, or reagent test ligands.

In this context, "irreversibly" and "irreversible" does not mean that the liposomes or lipid membranes can never be removed from the energy-emitting surface by any modality, but rather means that the liposomes or lipid membranes are expected to remain attached to the energy-emitting surface for the duration of the assay.

Usually the anchor molecules will be biotinated or otherwise modified before the liposome synthesis reaction, and then mixed with the appropriate liposome lipids, target membrane receptors, fluorescent labeled target membrane receptor binding proteins (if any), and detergents, and then dialyzed to form the completed liposome reagent.

Typically, a different liposome synthesis reaction will be required for each different target membrane receptor.

Surface Binding Methods

In general, liposomes will be bound to the energy-emitting surface by high affinity non-covalent bonds mediated by an intermediate set of linker-receptor groups. For example, as previously discussed, one possible type of intermediate linker-receptor group is a biotin-avidin linker. Alternative linker-receptor groups, such as antigen-antibody linkers, will also frequently be used. Usually, two different methods will be employed, one method used to simply anchor the liposome to the solid surface in an irreversible manner, and the other method used to bind the reagent ligands to the surface. These reagent ligands, in turn, can reversibly bind to the target membrane receptors.

In order to keep the liposome membrane far enough away from the energy-emitting surface, and avoid possible membrane rupture or lysis, it will often be preferable to place the anchor groups and reagent ligand groups on the end of extended hyrophilic tethers. This allows the liposome to be bound to the solid surface, but at a far enough distance to avoid lysis. An additional advantage of extended tethers is this allows the underside of the liposome to be freely accessible to external soluble test ligands, which is required for various drug and ligand-binding assays.

For tethering, methods such as the polyethyleneglycol-phospholipid conjugate methods of Wagner and Taum (*Biophysical journal* 79, 2000, pp 1400–1414) may be used. Other tethering methods include the methods of Adimoolim et. al., *J. Biol. Chem.* 273(49), 1998, 32561–32567, Mac-Beath and Schreiber, *Science* 2000, 289, 1760–1763; and Falsey, Renil et al. *Bioconjugate Chem.* 2001, 12, 346–353. Generally, any hydrophilic tethering means that has an effective length of between about 10 and 500 nm, and has appropriate surface binding and receptor binding groups, will suffice.

Note that the entire tether does not necessarily need to be hydrophilic. Rather the combination of the reagent-ligand and the tether must simply be hydrophilic enough so as to enable the tethered reagent-ligand to interact with the target membrane receptor in a way that closely mimics the binding of the untethered reagent ligand to the target membrane receptor. Thus a strongly hydrophilic reagent ligand can be used with a neutral or even a mildly hydrophobic tether. Similarly the reagent ligand does not necessarily need to be at the end of the tether. Rather, multiple reagent ligands can be placed at various distances along the tether, much as a single fishing line can contain multiple hooks. Alternatively the reagent ligand may be placed at some intermediate point on the length of the tether, rather than at the end.

To reduce the work involved in creating microarrays with a large number of different target membrane receptors, it is helpful to put the generic parts of the reagent onto the energy-emitting surface. Here, such a pre-prepared surface is called an "active" surface. An example of such a pre-prepared active surface is shown in FIG. 1.

FIG. 1 shows the details of a general-purpose "active" energy emitting surface constructed using general-purpose tethered reagents. Here an anchor receptor (1), such as avidin or strepavidin, that is capable of binding to the liposome's anchor groups, is bound to surface (5) by tether group (2). The surface also contains means to present reagent ligands to the liposome's target membrane receptors. These reagent ligands are presented so that the reagent ligands, while always bound to the energy-emitting surface, are capable of binding to the liposome's target membrane receptor in a reversible manner.

Typically, the means to present reagent ligands will be a reagent ligand receptor, such as an antibody (3), that in turn is bound to energy emitting surface (5) by tether group (4). This reagent ligand receptor is usually designed to bind to a reagent ligand with a bifunctional "bridge" structure. Here, one part of the bridge reagent ligand contains a haptein or epitope that binds to a receptor (3) (such as an antibody) on the surface (5), and the second part of the bridge contains the reagent ligand that binds to a liposome's target membrane receptor. Details of this "bridge reagent ligand" are shown in a later figure.

The anchor and reagent ligand receptors (1) and (3) will typically be intermixed together on the same locations on energy emitting surface (5), so that a single liposome will encounter significant amounts of each. The anchor and reagent ligand receptors will be tethered to the surface with tether groups (2) and (4), that are usually long enough (typically around 10–500 nm) so that the liposome is able to float a safe distance away from the surface. This gap also (during the subsequent test) allows test-ligands to easily permeate to the underside of the liposome.

The binding between the components on the active surface, and the components on the liposome reagent, are shown in 11–20. Here, an anchor receptor (11), such as avidin, tethered to the surface (15) by tether (12) binds to a liposome membrane anchor (21). This holds liposome (20) close to the energy-emitting surface. A reagent ligand receptor (13), such as an antibody, is tethered to the surface (15) by tether (14). This reagent ligand receptor then binds to the liposomes' target membrane receptor (22), usually through an intermediate bridge reagent ligand (not shown). Because the scale of the liposome is considerably larger than the scale of the other components, the liposome is drawn in an unnatural squashed configuration.

Microarray Preparation

If microarrays with large numbers of different target membrane receptors are desired, often it will be advantageous to prepare an active surface, similar to that shown in FIG. 1, in advance.

To prepare the microarray, the various liposome solutions are exposed to appropriate bridge reagent ligands, which bind to the target membrane receptors. The unbound bridge reagent ligands are then removed by washing or dialysis. The liposomes are then spotted onto the active surface by standard microarray spotting techniques, and the liposomes allowed to bind to the active surface via the anchor mechanisms. The target membrane receptors are usually also reversibly linked to the surface by way of the bridge reagent ligand link. If immediate use is not desired, the microarrays may be stored for later use by further treatment with appropriate fixative solutions, such as trehalose, glycerol, or other preservative solutions.

Figure 2:
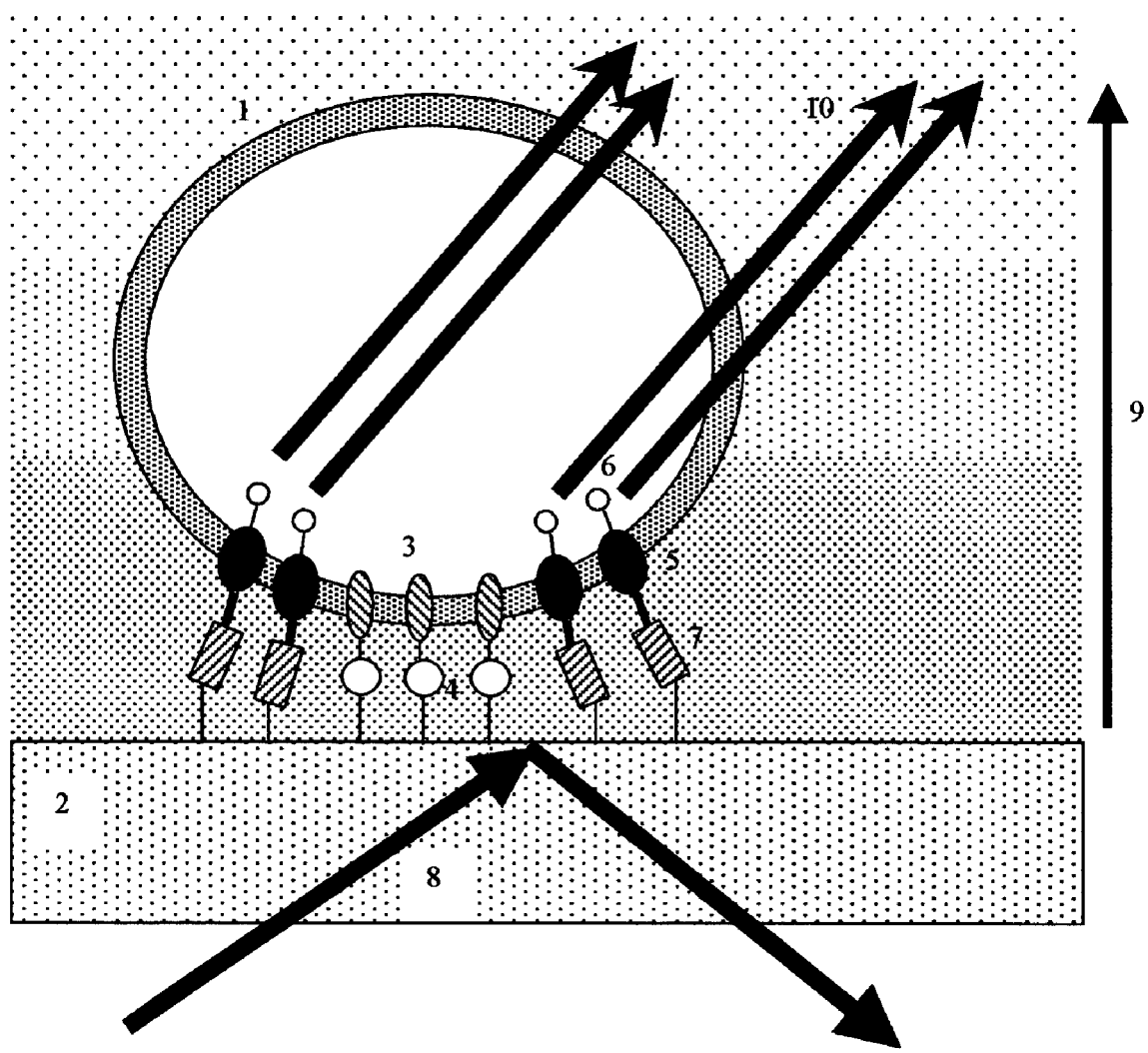
FIG. 2 shows a liposome in which the target membrane receptors, and a different set of anchor groups, are tethered to a surface, and observed by evanescent wave techniques.

FIG. 2 shows the details of a liposome bound to the surface of an evanescent wave-emitting surface. Here, the liposome (1) is anchored to the surface (2) by the interaction between an anchor protein, carbohydrate or lipid embedded into the liposome lipid bilayer (3). Surface bound anchor receptors then bind this component (4).

Note that although in this example, the liposomes are bound by an anchor set of receptor-ligand interactions; other surface binding methods may also be used. As one alternative, the liposomes may be physically entrapped next to the surface by a polymeric meshwork that has small enough pores to entrap the very large liposome, but large enough pores to enable test ligands to pass freely.

The liposome additionally contains a target membrane receptor (5), labeled with a detectable moiety (6), such as a fluorescent moiety. The energy-emitting surface contains a bound reagent ligand (7) capable of reversibly binding to the target membrane receptor (5).

In this example, the binding or non-binding of the target membrane receptor (5) to the reagent ligand (7) is detected by evanescent illumination (8). Here, the evanescent wave is strongest near surface (2), and rapidly decays as distance from surface (2) increases, so that there is an appreciable difference in illumination intensity between the top and bottom of vesicle (1), as is shown by arrow (9). Thus when the target membrane receptor (5) is bound to the reagent ligand (7), its detectable moiety (6) is exposed to a high intensity of evanescent illumination, and thus generates a strong fluorescent, luminescent, or other signal (10), which may be detected.

Figure 3:
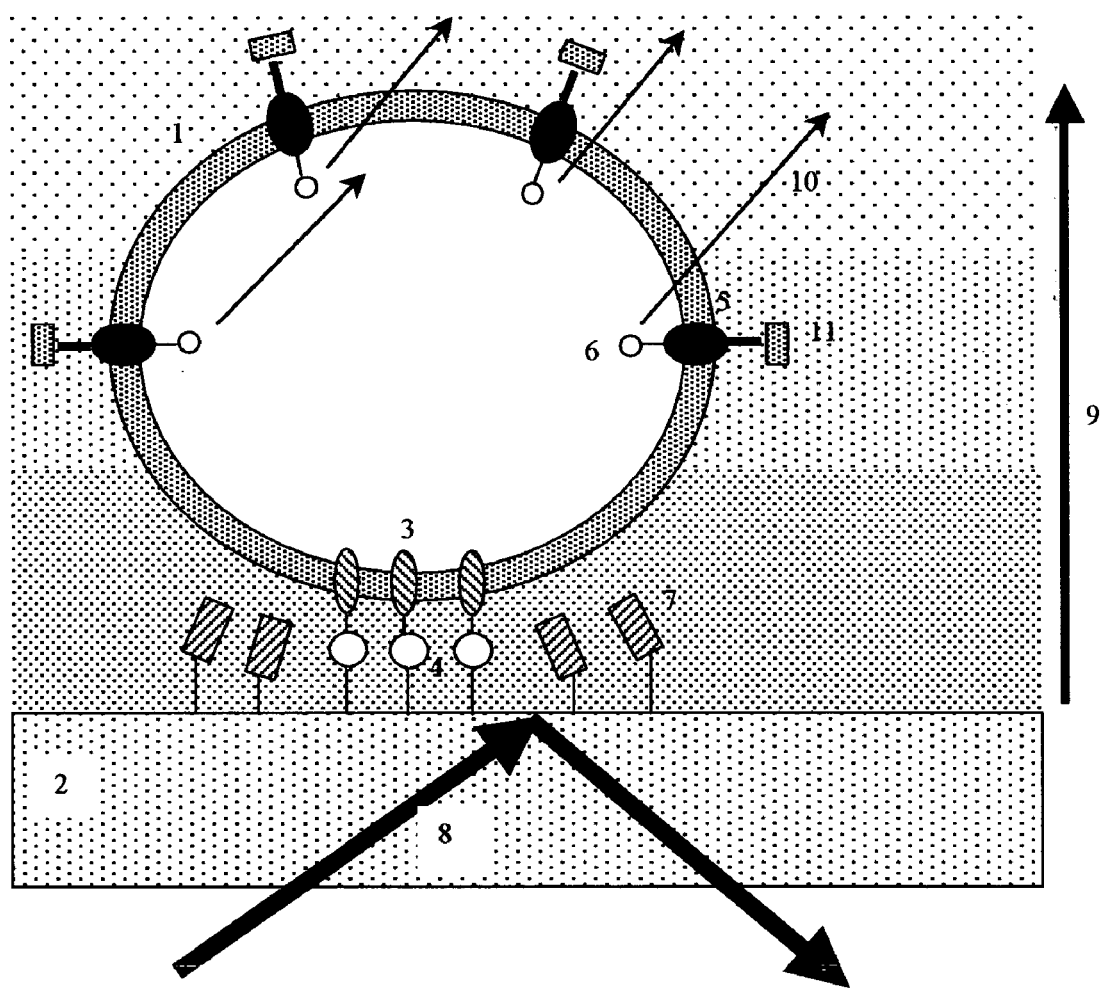
FIG. 3 shows a liposome in which the anchor groups remain tethered to the evanescent wave-emitting surface, but the distribution of the target membrane receptors has been perturbed by an external agent (such as a test-ligand).

FIG. 3 shows how alterations in the binding between the target membrane receptor (5) and the reagent ligand (7) may be detected. In this example, a test ligand (11), which acts to disrupt the association between the target membrane receptor (5), and the reagent ligand (7), is added to the system. (Here, this disruption proceeds by test ligand (11) binding to target membrane receptor (5), and thus blocking reagent ligand (7) from binding to target membrane receptor (5)). This disruption breaks the reversible bond between the target membrane receptor (5) and its reagent ligand (7), and as a result, the target membrane receptor (5) is now free to diffuse away from the energy-emitting surface (2), due to the fluid nature of the liposome lipid bilayer membrane (1). As a result, the detectable moiety (6) is now, on the average, a greater distance away from the energy-emitting surface (2), and is thus exposed to a significantly less amount of evanescent illumination (8, 9). As a result, the fluorescent, luminescent, or other signal generated by moiety (6) is now significantly decreased.

Regardless of the binding or non-binding of the target membrane receptor (5) to its reagent ligand (7), liposome (1) remains anchored to surface (2) by the interaction between the anchor embedded into the liposome lipid bilayer (3), and anchor receptors bound to the surface (4).

Note that for simplicity, FIGS. 2 and 3 show the case where the target membrane receptor (5) is initially bound to surface (2) by reagent ligand (7), and where the test ligand (11) acts to disrupt this binding. The opposite situation, where the target membrane receptor (5) is not initially bound to surface (2) by reagent ligand (7), and where the test ligand (11) acts to promote the binding the target membrane receptor (5) to reagent ligand (7), is also quite feasible.

Test ligand (11) can alter the binding between the target membrane receptor (5) and the reagent ligand (7) by many different means. Test ligand (11) may simply bind to target membrane receptor (5) directly and act to sterically hinder the binding between the receptor (5) and its reagent ligand (7), as is depicted in FIG. 2. Alternatively, test ligand (11) can alter binding between the target membrane receptor (5) and ligand (7) by other mechanisms, including binding to the reagent ligand (7) itself, or by altering the conformation or state of the target membrane receptor (5) or the reagent ligand (7). These alterations of conformation or state can be mediated by enzymatic modification, binding to allosteric receptor sites, etc.

Reference (Normalization) Signal Generation:

Because there are typically an uneven number of liposomes deposited in any given microarray zone, each with differing numbers of target membrane receptors, and each with detector moieties of varying efficiency, means to normalize the detectible signal to correct for all these variables are highly important.

To do this, a normalization signal must be generated that is not affected by the binding or non-binding of the target membrane receptors to the reagent ligands, but otherwise is a function of liposome number, target membrane receptor number, detector moiety efficiency, etc. The evanescent signal, which contains the target membrane receptor position information, as well as all the other variables, can then be adjusted by this normalization signal. The two signals can then be processed to report the target membrane receptor position information, free from distortion by the other test variables.

Figure 4:
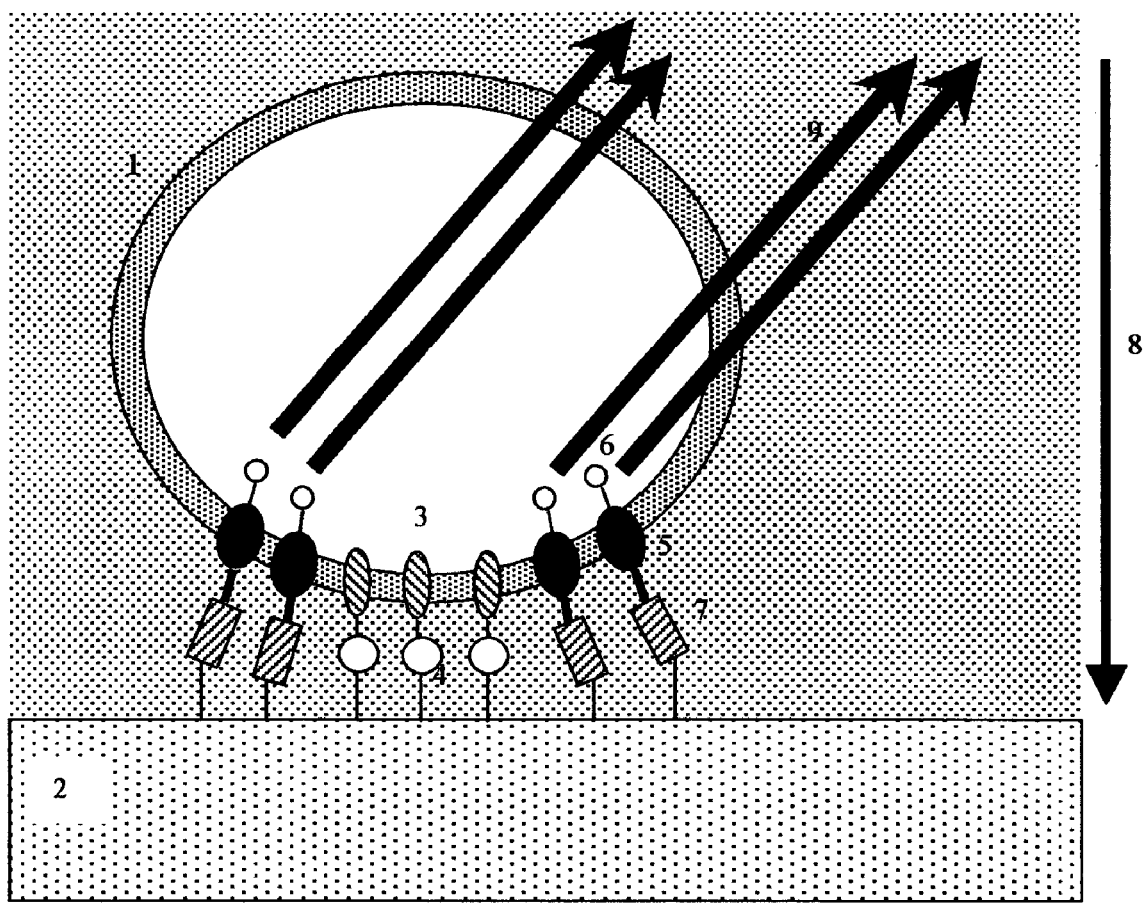
FIG. 4 shows a liposome in which the target membrane receptors and anchor groups are tethered to a surface, and are observed by normal fluorescence illumination.
Figure 5:
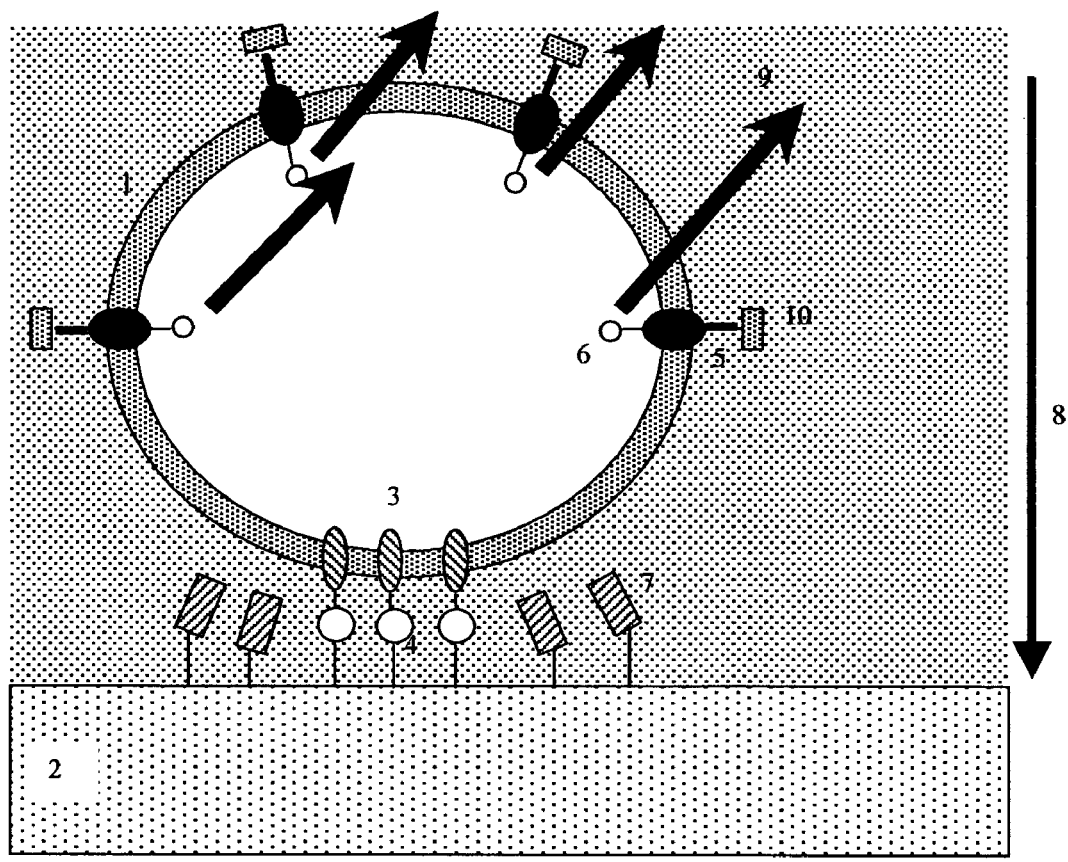
FIG. 5 shows a liposome in which distribution of target membrane receptors has perturbed by an external agent, again observed by normal fluorescence illumination.

FIGS. 4 and 5 show how normalization signals may be generated to help separate the evanescent signal depicted in FIGS. 2 and 3 from extraneous background signals. FIG. 4 shows the case where the target membrane receptor remains bound to the reagent ligand, and FIG. 5 shows the case where the binding between the receptor and ligand is disrupted by test ligands.

Here, for both FIGS. 4 and 5, a normalization signal is generated by exposing the liposomes (1) to a control source of fluorescence excitation energy that does not vary as a function of distance from surface (2). For this purpose, a normal fluorescence excitation energy source, such as epi-fluorescence illumination from a microscope objective above surface (2) may be used. This is shown by arrow (8). As a result, the energy (9) emitted by moiety (6) is relatively unaffected by the binding or non-binding of the target membrane receptor (5) to reagent ligand (7). This control or reference signal may be used to normalize, or otherwise process the signal depicted in FIGS. 2 and 3 to improve the sensitivity of the assay.

Non-evanescent control fluorescence excitation (8) may be generated by a variety of means, including epiilluminescence excitation from above surface (2), or fluorescence illumination from below surface (2) at an angle other than the critical angles where evanescence effects dominate.

Note that for FIGS. 4 and 5, as shown previously, liposome (1) is anchored to surface (2) by anchor (3) and anchor receptor (4). The test ligand that disrupts the binding between target membrane receptor (5) and reagent ligand (7) is shown in FIG. 5 as (10).

Figure 6:
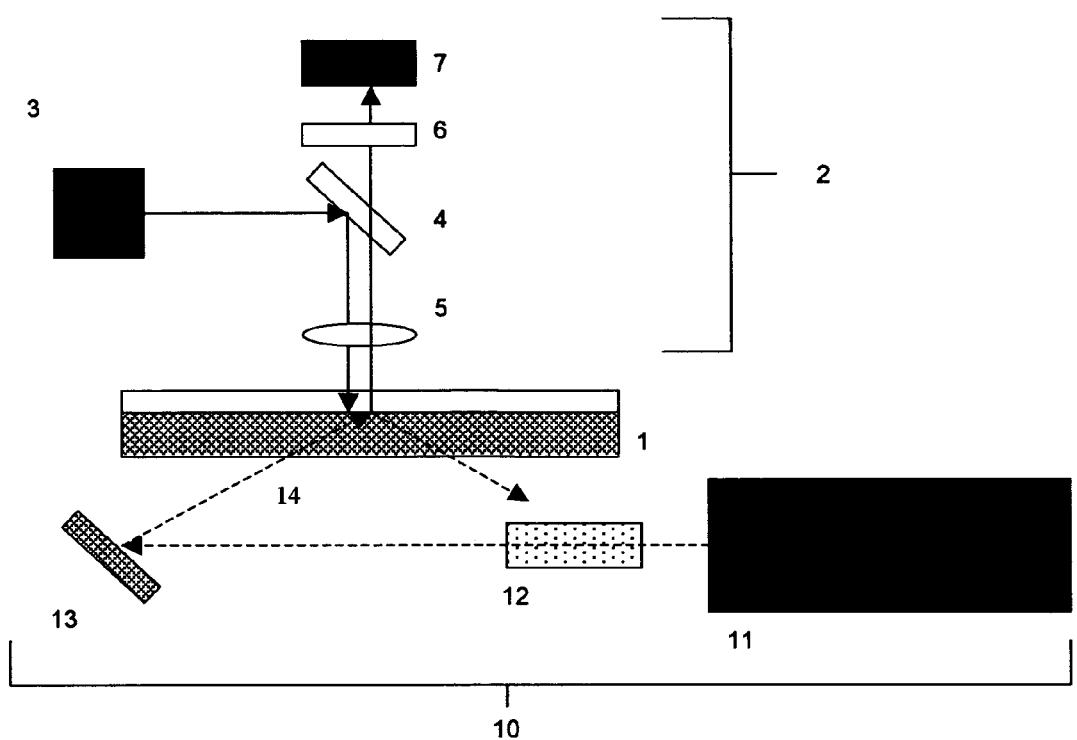
FIG. 6 shows a combination normal fluorescence (epifluorescent)/evanescent illumination instrument used to read the membrane receptor microarray

FIG. 6 shows a detail of the experimental apparatus used to obtain data from the membrane microarrays shown in FIGS. 2–5. Here the membrane microarray (1) is first illuminated by a fluorescent microscope (2) in order to obtain a normalization (reference) signal. This fluorescent microscope contains a fluorescent light source (3), which sends illumination through a bandpass mirror (4). This illumination is focused by objective (5) onto the microarray. The return fluorescence signal passes back through objective (5) though bandpass filter (6) and into a detector, such as a digital camera (7).

The evanescent illumination is provided by a second evanescent light source (10). Here, a second illuminator, such as a 488 nm argon laser (11), sends illumination through a collimator (12), which is directed by a mirror (13) to illuminate the underside of the microarray (1) with illumination (14) at the correct angle for evanescent illumination. The liposomes on the microarray (1) then emit an evanescent stimulated fluorescent signal which is imaged by the same optical system (5), (4), (6), (7) used to detect the normalization (reference) signal. Note that in operation, the reference fluorescent signal (used for normalization) and the evanescent fluorescent signal are obtained sequentially, rather than simultaneously.

Figure 7:
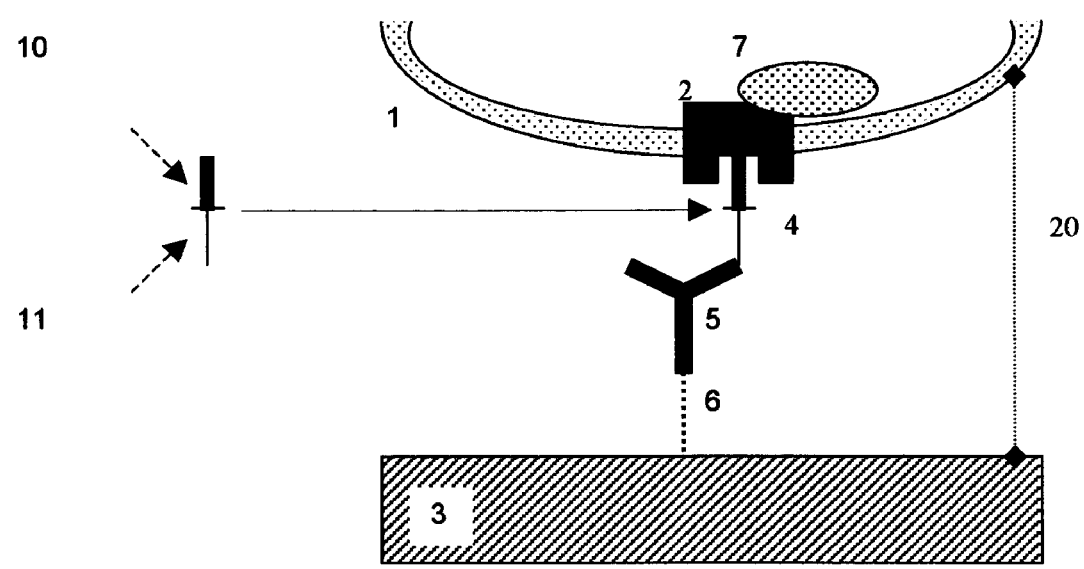
FIG. 7 shows how a target membrane receptor can be tethered to an energy-emitting surface by use of a bridging reagent ligand.

FIG. 7 shows the details of how a bridging reagent ligand may be used to bind a target membrane receptor to a microarray surface. Here liposome (1) has its target membrane receptor (2) bound to microarray surface (3) by a bridging reagent ligand (4) that binds both the membrane receptor (2), and a microarray surface bound receptor (5) (such as an antibody), tethered to microarray surface (3) by tether (6). Usually target membrane receptor (2) is labeled with a fluorescent moiety or reporter group (7).

The bridging reagent ligand (4) will often contain two groups. One group (10) is a reagent ligand that binds to target membrane receptor (2). A second group (11) contains means to link the bridging reagent ligand (4) to the microarray surface. In this example, the second group (11) contains a ligand (haptein, epitope, etc.) that binds to the microarray surface bound receptor (5). Here, this receptor (5) is an antibody against the bridge reagent ligand's haptein or epitope portion. Liposome (1) is additionally bound to microarray surface (3) by anchor means (20).

Figure 8:
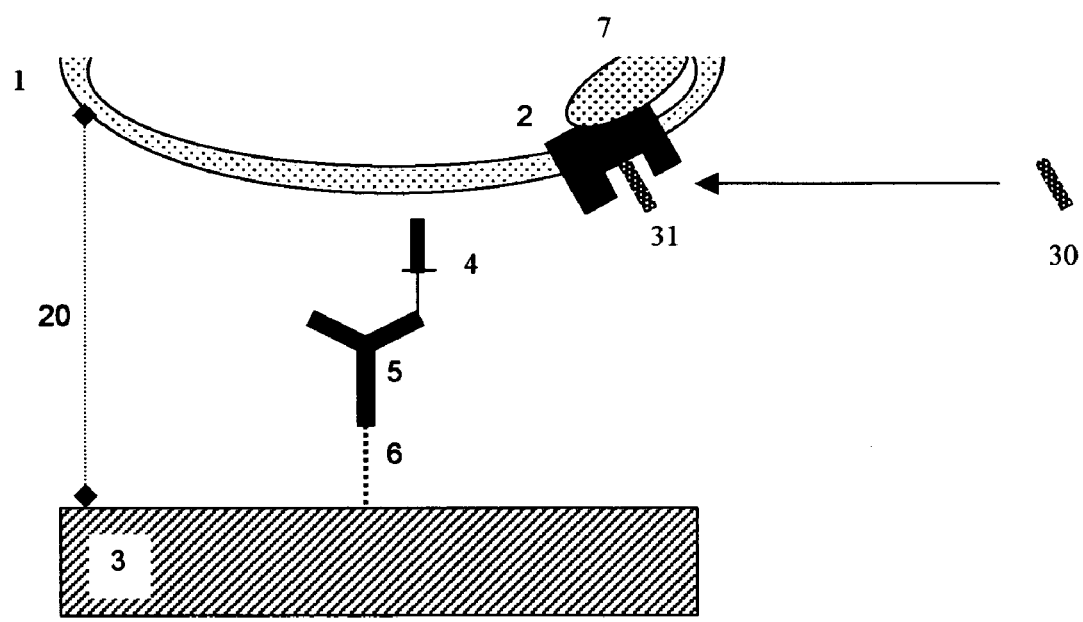
FIG. 8 shows how the coupling between target membrane receptors, and reagent ligands on an energy-emitting surface, can be disrupted by excess amounts of test ligands.

FIG. 8 shows how the binding between a target membrane receptor on a liposome, and a microarray surface receptor, normally mediated by a bridging reagent ligand, may be disrupted by the addition of excess amounts of a target ligand. Here liposome (1), previously had its target membrane receptor (2) bound to microarray surface (3) by a bridging reagent ligand (4) bound to a microarray surface bound receptor (5) (such as an antibody), tethered to microarray surface (3) by tether (6). As before, target membrane receptor (2) is labeled with a fluorescent moiety or reporter group (7). Also as before, liposome (1) is bound to microarray surface (3) by an anchor means (20).

Here, however, excess amounts of a test ligand (30) are added to the microarray. Test ligand (30) binds to target membrane receptor (2), as shown by (31). This disrupts the binding between target membrane receptor (2) and the bridging reagent ligand (4). As a result, target membrane receptor (2) is free to diffuse away from the microarray surface (3). As a result, fluorescent moiety or reporter group (7) also diffuses further away from the microarray surface (3), and thus receives correspondingly less evanescent illumination. Thus, if test ligand (30) binds to target membrane receptor (2), the evanescent excited fluorescent signal emitted by (7) will decrease in response to an increasing concentration of test ligand (30).

Figure 9:
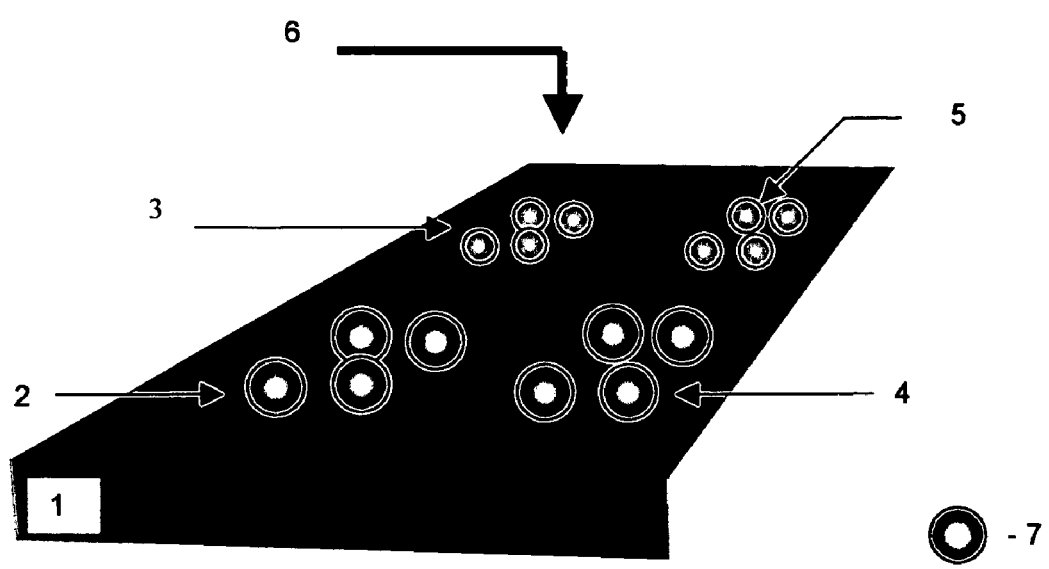
FIG. 9 shows a multiple element membrane receptor microarray

FIG. 9 shows a perspective view of a multi-element membrane receptor microarray. Here samples of different liposome preparations are spotted onto a microarray surface (1). Each liposome preparation is itself homogeneous. However different preparations will differ in variables such as the target membrane receptor type, type of bridging reagent ligand, lipid or cofactor composition, etc. For example, a hypothetical serotonin receptor microarray might contain one liposome population of $5\text{-HT}_{1A}$ receptors (2), a second liposome population of $5\text{-HT}_{2B}$ receptors (3), a third liposome population of $5\text{-HT}_{2C}$ receptors (4), a fourth population of $5\text{-HT}_6$ receptors (5), and so on. It could additionally contain either a homogeneous population of 5-HT bridging reagent ligands, such as 5-HT-haptein groups, or alternatively contain a population of different 5-HT bridging reagent ligands, comprised of different 5-HT analogs. This would allow discrimination between different test ligands with differing 5-HT receptor affinities.

A test ligand (6) is applied to the microarray, and differences in the evanescent illumination excited fluorescent signal are observed. Appropriate reference normalization signal data are also obtained. Often, microarray (1) will be a component of a flow-cell, so that different test ligand samples and controls may be applied to the microarray during the course of an experiment.

FIG. 9 also shows a single isolated liposome (7) as a scale reference.

Figure 10:
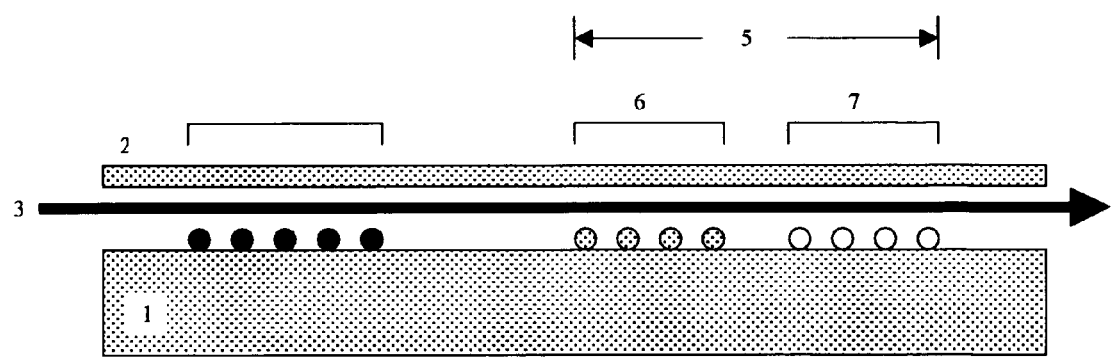
FIG. 10 shows a flow cell incorporating multiple types of target membrane receptors.

FIG. 10 shows a reusable flow cell containing a membrane liposome microarray (1), and a transparent cover (2). Samples, such as various drug discovery candidate test ligands, wash buffers, control samples, etc. flow through the cell on a sequential basis (3). Here, the flow cell contains both a drug screening section (4) containing samples of different target membrane receptors on different liposomes, and an ADMET section (5) that gives immediate feedback as to the potential suitability of a given candidate test ligand for drug use. Here, the ADMET section contains a portion with various cytochrome P450 drug detoxification membrane proteins (such as CYP3A4) on different liposomes (6), and a portion with various ABC drug transporter membrane proteins (such as P-glycoprotein) (7). Other ADMET detectors may also be added as appropriate.

EXAMPLES

Example 1

Evanescent Wave Calculations

Upon hitting a boundary between two media with different indexes of refraction, there is a critical angle in which light waves can either pass from the first media to the second media, or bounce back into the first media. At angles where light bounces back, part of the wave energy passes into the second media for a very short distance. This is called the evanescent wave. Evanescent wave techniques are commonly used in microscopy to help visualize regions where cultured cell membranes adhere to transparent supports.

In the common situation where light is passing from a glass or transparent support into an aqueous media, evanescent waves typically penetrate several hundred nanometers into the aqueous media. The wave decays in intensity at a rate of $$\text{Intensity} = I_o e^{(-z/d)}$$

Where $I_o$ is the illumination intensity at the support surface, z is the distance in nanometers above the support surface, and d is a constant (approximately 277 nanometers). (For these calculations, "e" will be approximated as 2.718.)

Thus for a roughly spherical 2 micron (2000 nm) diameter "large" liposome anchored to a microarray surface, the evanescent illumination intensity across the various portions of the liposome will be roughly as shown in Table 1 below:

TABLE 1

Evanescent illumination intensity across a 2 micron diameter liposome

| Liposomal quadrant | Average distance | Evanescent intensity |
| --- | --- | --- |
| Microarray bound base | 0 nm | 100% |
| Lower quarter (microarray side) | 250 nm | 40.56% |
| Lower-middle quarter | 750 nm | 6.67% |
| Upper-middle quarter | 1250 nm | 1.10% |
| Upper quarter | 1750 nm | 0.18% |

If all of the liposomes' fluorescently labeled target membrane receptors are bound to the surface by reagent ligands, then the liposome will fluoresce with a normalized intensity of 100%

By contrast, if the liposome's fluorescently labeled target membrane receptors are displaced from the surface by test ligands, the receptors are then free to randomly diffuse throughout the microarray surface. In this situation, the fluorescent intensity (roughly adjusted for variations in liposome surface area as a function of the quadrant size) is approximately as shown in table 2 below:

TABLE 2 fluorescence of membrane receptors uniformly distributed on an evanescently illuminated 2 micron liposome

| Liposomal quadrant | Illumination intensity | Apx. % surface area | Total |
|---|---|---|---|
| Lower quarter | 40.56% | 12.5% | 5.07% |
| Lower-middle quarter | 6.67% | 37.5% | 2.50% |
| Upper-middle quarter | 1.10% | 37.5% | 0.41% |
| Upper quarter | 0.18% | 12.5% | 0.02% |
| Total intensity | | | 8.01% |

Thus for a 2 nm liposome, the fluorescence of the randomly diffusing target membrane receptors, displaced from the surface by the test ligands, will decrease to about 8% of their initial surface-bound value. Larger diameter liposomes will produce correspondingly larger effects. For example, target membrane receptors distributed randomly over a 5-micron diameter liposome will decrease in intensity to only about 1.35% of their original surface-bound value.

Synthetic liposomes typically incorporate membrane proteins with 50% of the membrane receptors oriented on the "right side" ("N" terminal outside of the liposome), and 50% of the receptors on the "wrong side ("C" terminal outside of the liposome). This effect diminishes the signal only slightly, however. This is because the incorrectly inserted receptors randomly distribute throughout the liposome surface. Thus, for example, for 2 nm liposomes where both the "right side" and "wrong side" receptors are equally fluorescently labeled, the signal-to-noise ratio changes from 1/0.08 to (0.5+0.04)/0.08. This represents a decrease in the (bound/unbound) signal from a "good" ratio of 12.5:1, to a "still decent" 6.75:1.

Example 2

Signal Processing

As previously discussed, one of the most important signal enhancing techniques is signal normalization, using concurrent normal fluorescence (epifluorescent) illumination to provide a second reference, signal. Here the microarray spots are sequentially visualized by both evanescent illumination and epifluorescence illumination, and the evanescent signal is normalized by the epifluorescent signal. Since the epifluorescent signal is relatively unaffected by the position of the membrane proteins on the liposome, epifluorescence normalization corrects for many variables, including liposome spot density, labeling efficiency, and GPCR receptor concentration.

As an example of the issues that are involved in signal processing, consider the following model:

Any given microarray spot will have a variable number of liposomes "x", and a background signal "b", where b may be due to contaminating lysed lyposomes, autofluorescence, or other impurities in the reagent.

Each liposome, in turn, will generate an evanescent fluorescent signal, E, that is proportional to the relative ratio of the liposome's freely diffusing target membrane receptors ($R_f$) to the surface bound membrane receptors ($R_b$).

Thus $E=m(R_b/(R_f+R_b))$ where m is an efficiency constant.

In fractional terms: $R_f+R_b=1$ so therefore on a per liposome basis:

$$E=m(1-R_f).$$

So the total signal "S" from any given microarray spot will be proportional to the output per liposome, "E" times the number of liposomes, "x" so that:

$$S=m(1-R_f)x+b$$

To determine the percentage of free receptors, $R_f$ for any given microarray spot, the efficiency constant "m", the number of liposomes "x", and the background signal "b" must first be determined.

Here, the normal fluorescence (normalization) signal, "N" is useful, because this signal is unaffected by the ratio of bound to free target membrane receptors. Assuming that the normalization signal is done at the same wavelength, and that the instrument is previously calibrated to correct for any differing efficiencies between the normal fluorescence and evanescent signals, then:

$$N=m(R_f+R_b)x+b \text{ and since } R_f+R_b=1; \text{ then}$$

$$N=mx+b$$

Subtracting the evanescent signal from the normal fluorescent signal thus gives a result proportional to the number of free receptors, $R_f$, because:

$$N-S=mx+b-[m(1-R_f)x+b]$$

Thus: $N-S=m(R_f)x$

If the background signal, "b" is small, the fraction of unbound target membrane receptors $R_f$ per microarray spot can be found by dividing this result by the normal fluorescent signal, N, because according normal mathematical approximations, for any "b" that is small:

$$1/(1+b) \cong 1-b$$

Therefore: $m(R_f)x/(mx+b) \cong R_f - bm(R_f)x$ so for small values of b, where $bm(R_f)x$ is small, then:

$$R_f \cong (N-S)/N \qquad (1)$$

or alternatively $$R_b \cong 1-(N-S)/N \qquad (2)$$

In the case where the background signal "b" is large, or where additional precision is required, other signal processing methods may be used. One good way to do this is by incorporating the reagent spots into a flow cell. Here, each reagent spot may be calibrated by first exposing the reagent to a low-level control solution containing no test ligands, and determining a first control evanescent signal $S_1$. The flow cell is then exposed to a high level control solution containing a saturating concentration of test ligands, and a second control evanescent signal $S_2$ is obtained. Since for the zero test ligand control case, $S_1$, all the tethered membrane receptors are bound to the reagent ligands; so $R_f=0$, and $R_b=1$. Thus:

$$S_1=m(1-0)x+b; \text{ or alternatively } S_1=mx+b$$

By contrast, for the high test ligand control case $S_2$, all the tethered membrane receptors are free to diffuse away from the reagent ligands, so $R_f=1$ and $R_b=0$. Thus:

$$S_2=m(1-1)+b; \text{ or alternatively } S_2=b$$

Thus $S_1-S_2=mx;$

To determine the percentage of free ($R_f$) or bound ($R_b$) tethered membrane receptors for intermediate levels of unknown test ligands producing an evanescent signal $S_{test}$, the $S_{test}$ signal is processed using the data obtained from the S1 and S2 control data by $$S_{test}=m(1-R_f)x+b$$

and since $S_1-S_2$=mx; and $S_2$=b, then $$S_{test}=(S_1-S_2)(1-R_f)+S_2$$

Solving for the percentage of free receptors, $R_f$, for any given value of $S_{test}$ gives:

$$(S_{test}-S_2)/(S_1-S_2)=(1-R_f)$$

giving $$R_f=1-(S_{test}-S_2)/(S_1-S_2) \quad (3)$$

After the flow cell is calibrated with the low and high control solutions, and the $S_1$ and $S_2$ values are recorded for each reagent spot, the flow cell is then regenerated by flushing out the high control test ligands with excess buffer. After the regeneration cycle, the experimental test ligands are then added to the system, and the "$S_{test}$" experimental signal levels processed using the previously obtained $S_1$ and $S_2$ control values as in equation (3) above.

More complex processing schemes, involving combinations of normal flurorescence data, as well as high and low control flow cell data, are also possible.

Example 3

Studies with Model GPCR Target Membrane Receptors

Not all GPCR receptors bind drug ligands. Some, such as bacteriorhodopsin, act as sensors. Bacteriorhodopsin is a 7-transmembrane protein with well-understood properties. It is available in low cost and large quantities from a variety of commercial sources. It is easy to work with, and is often used for exploratory biophysical research. Here, methods to construct prototype membrane sensors using liposomes with fluorescent bacteriorhodopsin are described.

Preparation of Large Liposomes Containing Fluorescent Bacteriorhodopsin:

Bacteriorhodopsin from commercial sources can be labeled with the Alexa Fluor 488 fluorophore (a high efficiency fluorescent moiety), and incorporated into giant (5 micron) phospholipid vesicles (liposomes) following the methods of Kahya et. al (Kahya N, Pecheur E, de Boeij, W, Wiersma D, Hoekstra D, "*Reconstitution of Membrane Proteins into Giant Unilamellar Vesicles via Peptide-Induced Fusion*", Biophysical Journal, 2001 81: 1464–1474). In order to anchor these liposomes to energy emitting surface, trace amounts of N-biotinyl phosphatidylethanolamine, following the methods of Adimoolan et. al., (Adimoolam S, Jin L, Grabbe E, Shieh J, Jonas A, "*Structural and Functional Properties of Two Mutants of Lecithin-Cholesterol Acyltransferase* (T123I and N228K)", Journal of Biological Chemistry, 1998 272(49): 32561–32567), should be added to the liposome synthesis mix. The N-biotinyl phosphatidylethanolamine serves as a biotinated anchor group, which can be used to anchor the liposomes to an energy-emitting surface.

Active Energy Emitting Surface Preparation: An active energy-emitting surface can be constructed using microarray slides, following the methods of Macbeath (MacBeath G, Schreiber S "*Printing proteins as microarrays for high-throughput function determination*" Science, 2000, 289(5485):1760–3). Here, Bovine Serum Albumin (BSA) is used as a tether to link receptors to the microarray slide glass surface. This BSA linking method enables the microarray bound receptors to move somewhat, and additionally helps prevent direct contact between the liposome and the microarray surface. To do this, serum albumin is covalently bound to silane treated glass slides. This BSA layer, in turn, is activated with N,N'-disuccinimidyl carbonate. This activates the lysine, aspartate, and glutamate residues of the BSA, which in turn, are then available to react with surface amines on other proteins.

After activation, the BSA layer on the microarray surface is further reacted with a solution containing both strepavidin and IgG antibody. The strepavidin and IgG form covalent urea (or amide) links with the BSA, and thus become covalently attached to the microarray surface. After the reaction is complete, the slides are then rinsed with excess glycine to quench any unreacted groups.

Typically, in these experiments, the IgG antibody used is either rabbit anti-mouse IgG, or a control rabbit anti-goat IgG.

Binding of liposomes to microarray plates: Liposome solutions are typically stored in 40% glycerol following the methods of Macbeath, and spotted directly onto the microarray surface using a mechanical pin microarrayer device. The plates are incubated at 37° C. in a 95% humidity chamber for 1 hour, rinsed with phosphate buffered saline (PBS), and then stored in PBS at 4° C. until use. Often, it is useful to additionally spot 1-micron diameter Alexa Fluor 488 labeled latex microspheres to strategic microarray locations as evanescence/fluorescence controls. The liposomes are anchored to the microarray surfaces through the strepavidin—biotin link. By contrast, the fluorescently labeled bacteriorhodopsin target membrane receptors on the liposomes will not initially bind to the microarray plate because the rabbit anti-mouse IgG does not directly bind to bacteriorhodopsin.

Instrumentation: To observe the membrane microarrays, a standard Leitz fluorescence microscope, with a lower stage modified to allow for evanescent illumination, may be used. The microarray is alternately illuminated with the evanescent light source (see FIG. 6), and the fluorescence light source, and digital micrographs may be taken (Nikon Coolpix 995 in time exposure mode). The data is then downloaded and analyzed.

Characterization Experiments:

In one experiment, microarrays can be created in which the surface contains a first type of zone where the microarray-bound IgG is a rabbit anti-mouse antibody, and a second type of zone where the microarray bound IgG is a control rabbit anti-goat antibody. Alexa fluor 488 labeled bacteriorhodopsin liposomes can be spotted on both types of microarray zones, and allowed to anchor. The microarray will then be incubated with either a solution of monoclonal mouse anti-bacteriorhodopsin antibody or a control monoclonal mouse antibody at 37° C. for one hour, and observed by combination evanescence/fluorescence microscopy. Here, the only test condition where bacteriorhodopsin will tightly bind to the microarray surface is the zone where the mouse anti-bacteriorhodopsin antibody is bound to the rabbit anti-mouse antibody. The mouse anti-bacteriorhodopsin antibody binds to bacteriorhodopsin, and the antibody labeled receptors move in the fluid liposome membrane and become bound to the microarray surface-bound rabbit anti-mouse antibody.

The digital signals obtained from the microarray spots are averaged and normalized. The results can then be expressed according to equation (2): Bound bacteriorhodopsin $(R_b)$=1−[(Fluorescent signal−Evanescent signal)/ Fluorescent signal]

This will normally produce results, such as shown in table 3 below:

TABLE 3 binding of bacteriorhodopsin to microarray antibody zones

| | Added anti-bacteriorhodopsin antibody | |
|---|---|---|
| Antibody bound to microarray: | Mouse monoclonal anti-bacteriorhodopsin: % Bound bacteriorhodopsin $R_b$ | Control mouse monoclonal antibody: % Bound bacteriorhodopsin $R_b$ |
| Rabbit anti-mouse antibody zone | N = 100, E = 90, therefore $R_b$ = 1 − (100 − 90)/100 $R_b$ = 90% bound | N = 200, E = 20, therefore $R_b$ = 1 − (200 − 20)/200 $R_b$ = 10% bound |
| Control rabbit antibody zone | N = 150, E = 15, therefore $R_b$ = 1 − (150 − 15)/150 $R_b$ = 10% bound | N = 50, E = 50, therefore $R_b$ = 1 − (50 − 5)/50 $R_b$ = 10% bound |

Note that in the above example, the amount of material per spot, as shown by the normal fluorescent intensity "N", is shown varying from 50 to 200 units. However normalization methods can compensate for these variations.

Adding excess control monoclonal antibody to the microarray will typically reverse the bacteriorhodopsin binding. In an alternate version of this experiment, which simulates the use of bridging reagent ligand techniques, fluorescent bacteriorhodopsin liposomes can first be incubated with monoclonal mouse anti-bacteriorhodopsin antibody, and then bound to strepavidin+rabbit anti-mouse coated zones on microarray active surfaces. Here, the liposomes will anchor to the microarray surface by the strepavidin-biotin links. The mouse monoclonal antibody, which itself is bound to the liposome's bacteriorhodopsin target membrane receptors, in turn binds to the rabbit anti-mouse antibody zone on the microarray surface. The fluorescent bacteriorhodopsin target membrane receptors move in the fluid liposome membrane and become bound to the surface, resulting in a larger evanescent excited fluorescence signal.

This binding can be broken by an excess of control mouse monoclonal antibody (e.g. without bacteriorhodopsin binding activity). The control antibody binds to the surface bound rabbit anti-mouse antibody, and saturates all of its anti-mouse binding sites. Thus the mouse anti-bacteriorhodopsin antibody on the liposome can no longer bind to the surface, and the fluorescent bacteriorhodopsin molecules are now free to diffuse randomly throughout the entire liposome surface, resulting in a drop in the evanescent excited fluorescent signal. Here, the control antibody has a competitive effect similar to the competitive effect of the test ligands discussed previously. An example of this type of competition experiment is shown in table 4 below:

TABLE 4 effect of competition binding

| | Added control mouse antibody | |
|---|---|---|
| Antibody bound to microarray: | Excess mouse antibody % Bound bacteriorhodopsin $R_b$ | No excess mouse antibody % Bound bacteriorhodopsin $R_b$ |
| Rabbit anti-mouse antibody | N = 50, E = 5, therefore $R_b$ = 1 − (50 − 5)/50 $R_b$ = 10% bound | N = 100, E = 90, therefore $R_b$ = 1 − (100 − 90)/100 $R_b$ = 90% bound |
| Control rabbit antibody | N = 200, E = 20, therefore $R_b$ = 1 − (200 − 20)/200 $R_b$ = 10% bound | N = 150, E = 15, therefore $R_b$ = 1 − (150 − 15)/150 $R_b$ = 10% bound |

As before, normalization techniques may be used to compensate for the effect of varying spot intensity.

Table 4 shows that excess control mouse monoclonal antibody can displace the surface bound mouse anti-bacteriorhodopsin antibody. Thus the fluorescent bacteriorhodopsin molecules on the liposome are free to diffuse away from the microarray surface, resulting in a smaller evanescent excited fluorescent signal.

Example 4

Construction of Membrane Receptor Microarrays for Drug Discovery Purposes

A drug discovery membrane receptor microarray may be constructed using commercially available cloned membrane receptors and bridge reagent ligands. Here, a prototype multi-element microarray containing various types of serotonin (5-HT) receptors is described.

Serotonin receptors play an important role in the nervous system, and are responsible for a variety of behavior disorders including appetite, depression, and obesity. This receptor family is the subject of much intense drug discovery effort by the pharmaceutical industry, and methods to facilitate such discovery methods are of large practical interest.

Serotonin membrane receptor microarrays can be constructed using commercially available serotonin GPCR receptors such as 5-$HT_{1A}$, 5-$HT_{2B}$, 5-$HT_{2C}$, 5-$HT_6$, and 5-$HT_7$. These are available from the Euroscreen corporation, and other companies. As a control, the microarray may additionally contain a number of "non-target" receptors from an entirely different GPCR receptor family, such as the dopamine receptor family. These non-target receptors can serve as a control, and also help detect unwanted target ligand cross reactions.

For these prototype microarrays, pure (no cofactor) GPCR receptors may be used. However more physiologically realistic systems may be created by incorporating additional receptor cofactors (such as $G\alpha$, $\beta$, and $\gamma$-proteins, etc.) into the liposome preparations as appropriate. Some of the considerations as to the physiological impact of such cofactors is discussed in Brys et. al., *Reconstitution of the Human 5-HT1D Receptor-G-Protein Coupling: Evidence for Constitutive Activity and Multiple Receptor Conformations*, Molecular Pharmacology 2000, MOL 57:1132–1141).

GPCR Fluorescence Labeling Methods: For these purposes, direct fluorophore labeling by chemical means (such as the Alexa Fluor 488 labeling method discussed for the bacteriorhodopsin examples), although often useful, may sometimes be less preferred in cases where such labeling damages the receptors. Use of GPCR-fluorescent protein fusion products, such as GPCR-green fluorescent protein, or GPCR aquelorin products, although quite feasible, is labor intensive because this requires the creation of a different fusion product for each microarray element. As a result, use of modified forms of natural wide-specificity GPCR binding proteins, such as fluorescent β-arrestin (Ferguson, S., Barak, L., Zhang, J., Caron, M, "*G-protein-coupled-receptor regulation: role of G-protein-coupled-receptor kinases and arrestins*" Can. J. Physiol. Pharmacol. 1996, 74: 1095–1110) may be useful. This is because β-arrestin binds to the vast majority of the various GPCR proteins.

To generate a higher fluorescent or luminescent signal, use of fluorescent micro particles may be advantageous. Such particles, such as quantum dots (quantum dot corporation, Hayward Calif.), fluorescent latex micro spheres (transfluospheres, Molecular Probes Inc., Eugene Oreg.), etc. typically have diameters between about 10 nm and 100 nm, contain large numbers of signal generating molecules, and can be labeled with antibodies specific to the cytoplasmic side of various target membrane receptors, or target membrane receptor binding proteins. Use of such micro particle based label moieties can produce a more intense signal requiring less amplification and lower cost detection equipment.

Liposome synthesis: in this example, liposomes are synthesized by dialysis of detergent solubilized purified 5-HT receptors, liposome lipids, biotinated lipids (for microarray anchoring purposes), and fluorescent labeled wide-specificity GPCR binding proteins such as GFP-β-arrestin. This results in the creation if intact liposomes containing labeled serotonin receptors and suitable anchor groups. A different synthesis is done for each different serotonin receptor.

Bridge Reagent Ligands: In order to be useful for drug discovery purposes, the liposome's fluorescent serotonin GPCR receptors must bind to the microarray surface in the absence of competing test ligands, and dissociate from the surface in the presence of competing test ligands. As previously discussed, this can be done by using bridge reagent ligands. These are composed of a conjugate of a ligand that binds to the appropriate serotonin GPCR receptors, and a chemical group (such as a haptein) that binds to a haptein-receptor (usually an anti-haptein antibody) that is tethered to the microarray surface.

Although many different types of haptein (or other tethering) groups may be used for the 5-HT-haptein conjugates, use of the coumarin group is particularly convenient because a number of 5-HT-coumarin conjugates have been previously synthesized by other workers. Previous synthesis of this type have been reported by Friedrich et. al. ("*Investigation of the 5-HT3 Serotonin Receptor Using Novel Fluorescent Ligands*", Ecole Polytechnique Federale de Lausanne (poster session)), and a number are commercially available from Tocris Cookson Inc., and other vendors. Although the coumarin group is itself fluorescent, it is excited by shorter wavelengths than those used by the GPCR label fluorophores, and thus cross-talk effects are minimal. These coumarin groups can be used as hapteins because they are antigenic, and anti-coumarin antibodies are commercially available.

Here, the liposome preparations are exposed to the 5-HT-coumarin bridge reagent ligands, and the excess (unbound) bridge reagent ligands are then removed by washing. The liposomes+bound bridge reagent ligands are then spotted onto different locations on an active microarray surface.

Active Microarray Surface Preparation: The microarray surface chemistry plays a critical role for evanescent-liposome microarrays. Here there are two general considerations. The first is that both the microarray's anchor receptors and reagent ligand receptors should preferably be attached to the surface by tether groups that allow a sufficient aqueous gap between the fragile liposome and the surface so that the liposome does not lyse upon the surface, and so that test-ligands can penetrate to the underside of the anchored liposome.

For these purposes, the polyethylene glycol tethers of Vermette et. al. are useful (Vermette P, Meagher L, Gagnon E, Griesser H J, Doillon C J "*Immobilized liposome layers for drug delivery applications: inhibition of angiogenesis*" J Control Release 2002, 80(1–3):179–95). This work has shown that the use of polyethylene glycol-biotin linkers improves the lifetime of intact liposomes on plastic surfaces. Other hydrophilic tethering molecules may also be used, however.

For these experiments, appropriate active surfaces can be created by preparing a microarray surface containing a mixture of avidin (or strepavidin) groups bound to the surface by a polyethylene glycol tethers, and a mixture of anti-coumarin antibodies, also bound to the surface by a polyethylene glycol tether.

To make a useful drug discovery microarray reagent, a combination of liposome preparations containing different populations of 5-HT receptors, control receptors, and different types of bridge reagent 5-HT ligands is spotted onto a microarray surface, creating a prototype microarray reagent as shown in table 5 below:

TABLE 5 prototype serotonin receptor microarray

| Receptor | Bridge Reagent - Ligand | Alternate 5-HT Bridge Reagent Ligand 1 | Alternate 5-HT Reagent Ligand 2 |
|---|---|---|---|
| $5\text{-HT}_{1A}$ | 5-HT-coumarin | Low affinity analog | High affinity analog |
| $5\text{-HT}_{2B}$ | 5-HT-coumarin | Low affinity analog | High affinity analog |
| $5\text{-HT}_{2C}$ | 5-HT-coumarin | Low affinity analog | High affinity analog |
| $5\text{-HT}_{6}$ | 5-HT-coumarin | Low affinity analog | High affinity analog |
| $5\text{-HT}_{7}$ | 5-HT-coumarin | Low affinity analog | High affinity analog |
| $D_1$ (dopamine) | Dopamine-coumarin | Low affinity analog | High affinity analog |
| $D_2$ long (dopamine) | Dopamine-coumarin | Low affinity analog | High affinity analog |

Prototype Drug Discovery Assays:

The microarray shown in table 5 may then be incorporated into a miniature flow-cell, constructed using a microscope slide, appropriate spacers, tubing, and a cover slip so that different reagents may be slowly flowed over the microarray. The microarray, in turn, is mounted onto a dual evanescent/fluorescent detection apparatus, similar to that shown in FIG. 6. The microarray may then be calibrated by exposing it to the appropriate control solutions with zero and high levels of 5-HT, as discussed previously.

After the high control solution has been flushed out, and the microarray target membrane receptors restored to their no-target-ligand, surface-bound configuration, samples of appropriate test ligands can then be applied to the microarray, and the microarray response characterized.

As an example, consider a test-ligand that is a 5-HT analog with highest affinity for the $5\text{-HT}_{2C}$ receptor, and relatively low affinity for the other 5-HT receptors. Its response in the membrane microarray flow cell may look like table 6 below:

TABLE 6 binding of a 5-HT$_{2C}$ specific test ligand
to a serotonin receptor microarray

| Receptor | Bridge Reagent | Alternate high affinity 5-HT Bridge Reagent | Alternate low affinity 5-HT Bridge-Reagent |
|---|---|---|---|
| 5-HT$_{1A}$ | R$_b$ = 90% | R$_b$ = 95% | R$_b$ = 70% |
| 5-HT$_{2B}$ | R$_b$ = 90% | R$_b$ = 95% | R$_b$ = 70% |
| 5-HT$_{2C}$ | R$_b$ = 10% | R$_b$ = 20% | R$_b$ = 5% |
| 5-HT$_6$ | R$_b$ = 90% | R$_b$ = 95% | R$_b$ = 70% |
| 5-HT$_7$ | R$_b$ = 90% | R$_b$ = 95% | R$_b$ = 70% |
| D$_1$ (dopamine) | R$_b$ = 100% | R$_b$ = 100% | R$_b$ = 100% |
| D$_2$ long (dopamine) | R$_b$ = 100% | R$_b$ = 100% | R$_b$ = 100% |

In this example, the experimental target-ligand displaces the 5-HT$_{2C}$ target membrane receptors the most. The example also shows that the target ligand also has mild cross reactivity with other members of the 5-HT receptor family, but no cross-reactivity whatsoever with dopamine family target membrane receptors.

ADMET Assays:

Example 5

P-glycoprotein Transport Assay

Although much of the previous discussion, as well as the serotonin receptor example, have focused on assays in which the surface-bound reagent-ligand binds to the target membrane receptor via intermediate bridge reagent ligands, this need not always be the case. Sometimes the surface may contain a tethered "non-drug-like" reagent ligand, such as an antibody, that directly binds to the target membrane receptor.

As an example of this alternative method, consider P-glycoprotein assays. P-glycoprotein is an ABC (ATP binding cassette) protein that plays a major role in pumping drugs out of cells. Indeed, hyperexpression of P-glycoprotein is an important mechanism of cancer cell resistance to anticancer drugs. In this role, it is often referred to as the "multidrug resistance protein 1", or MRP1. Due to its major role in controlling drug transport in the body, characterization of an experimental test ligand's ability to be transported by P-glycoprotein is an important ADMET test.

P-glycoprotein is a transmembrane protein that pumps drugs out of the cell, against a concentration gradient, by the hydrolysis of ATP. The transport process involves several steps in which the protein binds the drug, changes conformation to expel the drug, binds ATP, and then regenerates it's original conformation. Previous workers, (Nagly et. al., *P-glycoprotein conformational changes detected by antibody competition*, Eur. J. Biochem. 268, 2416–2420 (2001)) have produced monoclonal antibodies, such as UIC2, that bind to the conformation that the P-glycoprotein assumes the presence of P-glycoprotein transport substrates or inhibitors. The antibodies do not bind to the conformation that P-glycoprotein assumes in the absence of such transport substrates or inhibitors.

Such conformational sensitive antibodies may be used as reagent ligands to perform P-glycoprotein ligand transport assays in the evanescent liposome format. Here, as always for this format, P-glycoprotein needs to be labeled with a detectable moiety. To do this, a number of methods are suitable, such as the green fluorescent or cyan fluorescent protein labels. Here, the methods of Rajagopal et. al., (*In vivo analysis of human multidrug resistance protein 1* (MRP1) *activity using transient expression of fluorescently tagged MRP1* Cancer Res 2002 Jan. 15;62(2):391–6), may be used.

Next, the fluorescently tagged P-glycoprotein molecules are reconstituted into artificial liposomes, along with suitable anchor molecules (such as the biotinated lipids discussed previously). Here again, a variety of reconstitution methods, such as the methods of Dong et al. (*Efficient purification and reconstitution of p-glycoprotein for functional and structural studies*, J. Biol. Chem. 271 (46) 28875–28883, 1996), may be used.

A P-glycoprotein conformation sensitive antibody, such as UIC2 (a mouse antibody), serves as the reagent ligand for this assay. This antibody may be either tethered directly to the assay surface, as described previously, or else tethered indirectly by binding to an active surface tethered anti-antibody (second antibody).

The liposomes containing the fluorescent-labeled P-glycoproteins are then applied to the detector surface (which will usually be part of a flow cell, or flow cell component, such as a capillary tube), and their anchor groups are allowed to bind.

Since the transport ability of P-glycoprotein is ATP dependent, appropriate levels of ATP and magnesium (required for ATP hydrolysis) may also be added to the assay reaction buffer at various times during the assy.

Over the course of the assay, the distribution of the P-glycoprotein molecules will vary. In the absence of P-glycoprotein binding test ligands, the fluorescently labeled P-glycoprotein molecules will not bind to the surface bound, UIC2 like, antibody. They will randomly diffuse throughout the liposome membrane, and thus produce a relatively small evanescently stimulated fluorescent signal. By contrast, in the presence of a P-glycoprotein binding test ligand, the fluorescent-labeled P-glycoprotein molecules will bind to the UIC2 like antibody, and thus distribute close to the evanescent wave-emitting surface. This will produce a relatively large evanescently stimulated fluorescent signal. Test ligands that bind to P-glycoprotein can thus be quickly detected. These test ligands can then be flagged for further study.

Example 6

Cytochrome P450 Binding Assay

The evanescent-liposome techniques disclosed here can also be used to study the binding of enzyme substrates to membrane bound enzymes, such as members of the cytochrome P450 family. This family of membrane proteins is responsible for the majority of drug breakdown or metabolism in the body. Different individuals possess different isozymes of cytochrome P450, and thus differ in their ability to metabolize any given drug. Thus an important part of ADMET analysis is characterizing the interaction between a drug candidate, and the various cytochrome P450 enzymes.

Previous work has shown that cytochrome P450 substrate ligands (type I ligands) may be used to displace cytochrome P450 from surface bound triazole-based general P450 inhibitors (type-II ligand) (Winter et. al., "*A microsomal ecdysone-binding cytochrome P450 from the insect Locusta migratoria purified by sequential use of type-II and type-I ligands*" Biol Chem 2001 November; 382(11): 1541–9). In this earlier work, this displacement was used in affinity columns to purify cytochrome P450 enzymes of interest.

However this displacement technique may also be utilized for the evanescent liposome methods of the present invention.

Here, cytochrome P450 binding assays may be performed by testing the ability of an unknown test ligand to displace a given cytochrome P450 target membrane receptor from an evanescent surface bound P450 inhibitor, which serves as a reagent ligand. Here, as in the work of Winter, this reagent ligand may be a triazole-based general P450 inhibitor (type-II ligand).

To do this, as always, the Cytochrome P450 family target membrane receptors need to be labeled. A good way to do this is by fusion with green fluorescent protein, following the methods of Rainov et. al. "*A chimeric fusion protein of cytochrome CYP4B1 and green fluorescent protein for detection of pro-drug activating gene delivery and for gene therapy in malignant glioma*" Adv Exp Med Biol 1998;451: 393–403. Such hybrid fusion cytochrome P450—green fluorescent protein hybrids have been shown to retain their proper spectrum of enzymatic activity.

Liposome synthesis: fluorescent cytochrome P450, liposome lipids, and appropriate anchor groups, may be incorporated into liposomes using a variety of methods, including the detergent dialysis methods described previously. Since cytochrome P450 requires activation with cytochrome P450 reductase, and cofactors such as NADPH, NADH, FAD, FNM, etc., these cofactors may additionally be incorporated into the liposome and/or the reaction buffer as appropriate.

In the absence of test ligands with cytochrome P450 binding ability, the fluorescent cytochrome P450 target membrane receptors will bind to the surface bound cytochrome P450 inhibitors, and thus exhibit a relatively strong level of evanescent wave stimulated fluorescence. In the presence of test ligands with cytochrome P450 binding ability, however, the fluorescent cytochrome P450 target membrane receptors will become displaced from the surface bound inhibitor. This will result in a decrease in the amount of evanescent wave stimulated fluorescence.

Test ligands that bind to various cytochrome P450 family members of interest can thus be quickly detected. These test ligands can then be flagged for further study.

Example 7

Composite Test Devices

In many embodiments, it may be desirable to combine one or more test elements of the present invention with micro-fluidic switch elements. Such micro-fluidic switches can be used to dynamically redirect the passage of a test ligand through a multiple of different detector elements, depending upon the results of earlier tests in the series. Usually, the micro-fluidic switches and detection elements will be computer controlled.

As an example, consider a multi-element device consisting of a series of target receptor binding elements, a series of non-target receptor elements, a series of ADMET detector elements, and a high-performance, but low throughput, test ligand analyzer such as a mass spectrometer. Here, micro fluidic switches may direct the passage of the test ligand through the system. As an example, depending upon the results of the binding element portion of the system, a non-target binding test ligand may be directed to a waste container, and subsequent non-target and ADMET analysis skipped. Those test ligands with appropriate target and non-target binding properties may be directed to the ADMET section. In turn, those test ligands with appropriate ADMET characteristics may be directed to a general purpose, high-performance, test ligand analytical system, such as the mass spectrometer example given previously. This way, promising test ligands may be almost instantly identified and characterized.

Such micro fluidic-switched, multi-element methods, may also be desirable for speeding up test throughput. Typically, a set of unknown test ligands will only contain a few members with the ability to bind to the desired set of target membrane receptors. Since usually, no further analysis of test ligands without the desired binding capability is necessary, further analysis may be skipped and these test ligands may be discarded. Here, micro fluidic switching elements enable the creation of networked multi-element drug detection flow cell devices. Here, a large number of test ligands is screened in many different reaction cells for the desired reactivity to appropriate target membrane receptors. Those that are seen to have the appropriate binding capability are then directed by micro fluidic switches to a smaller number of reaction cells, where a second stage of binding to non-target membrane receptors is assessed. Those few test ligands that pass this second stage test are then directed by micro fluidic switches to a relatively small number of ADMET flow cell sensors. At any point in the analysis, interesting test ligands can be diverted to a general purpose high performance ligand analyzer, such as a mass spectrometer.

In this way, a high-performance micro-analytical drug discovery system may be created. Such a system could work using ultra small quantities of materials, such as the material created from a single combinatorial synthesis bead, and could significantly reduce the amount of materials, time, and effort required for the drug discovery process.

Example 8

Composite Test Supports

Figure 11:
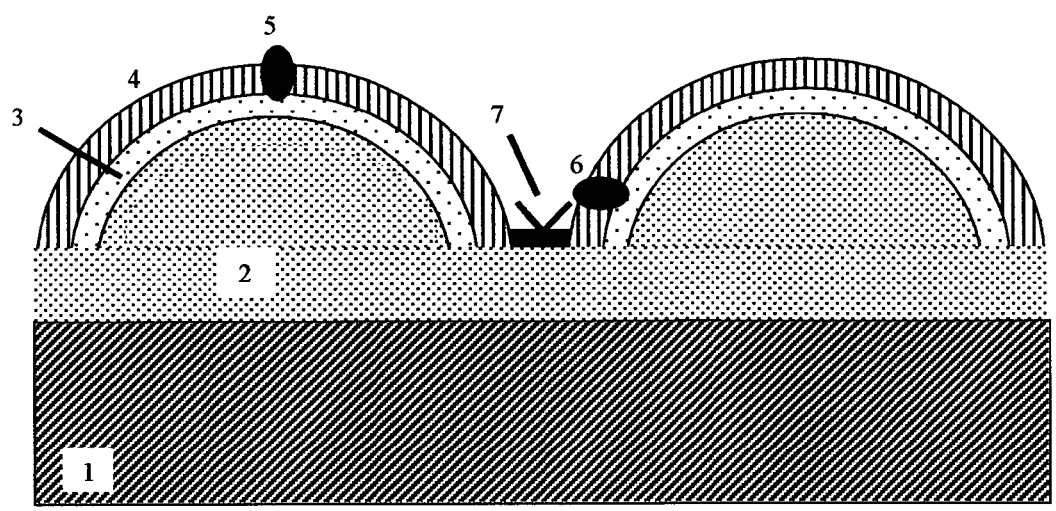
FIG. 11 shows an example of a composite support material.

As previously discussed, use of composite support materials may be desirable in some cases. FIG. 11 shows an example of such a composite support. An underlying flat energy emitting material (1), such as glass or plastic, that has an index of refraction significantly different from the assay's aqueous media, is covered with a variable thickness coating of a different transmission material (2), such as a water permeable porous polymer, that has an index of refraction substantially similar to the aqueous media. In this example, the different transmission material (2) has been deposited in a configuration that creates a variable distance from the underlying support material (1) by replica molding, photolithography, or other process. Evanescent waves coming from the interface between energy emitting material (1) and transmission material (2) thus are attenuated to a variable extent depending upon the local thickness of transmission material (2). If transmission material (2) is chosen to have an index of refraction similar to the assay's aqueous media outside of material (2), this evanescent wave will continue to propagate through material (2) and the boundary between material (2) and the assay's aqueous media in an essentially undisturbed manner. As a result, the intensity of the evanescent wave in the assay's aqueous region outside of material (2) will vary as a function of material (2)'s thickness.

In some cases, it may be useful to modify transmission material (2) to enable it to support (and irreversibly anchor) lipid bilayers by using silane-polyethyleneglycol-lipid as a cushion and covalent linker layer (3), following the methods of Wagner and Tamm (*Tethered Polymer-Supported Planar Lipid Bilayers for Reconstitution of Integral Membrane Proteins: Silane-Polyethyleneglycol-Lipid as a Cushion and Covalent Linker*, Biophysical Journal Volume 79 September 2000 1400–1414), or equivalent methods. The net effect is to produce a bumpy support surface (2,3) that anchors a lipid bilayer at a variable distance from the underlying energy-emitting surface (1). This variable height lipid bilayer (4) contains laterally mobile target membrane receptors (5, 6), which are labeled with reporter groups. Because they are laterally mobile, these target membrane receptors can freely diffuse to various locations far away from (5) or close to (6) the energy-emitting surface (1).

The composite test support may further contain regions where tethered reagent ligands are bound (7). A replica molding, photolithographic, or other process may be used to create such regions. Ideally such tethered reagent-ligand regions (7) will be located either far away from, or close to, energy-emitting surface (1), so as to maximize the signal difference between the reagent-ligand bound (6) and unbound (5) state of the target membrane receptors. The net effect is to create the same type of membrane receptor assay as discussed previously, but with an alternate geometry that does not necessarily require the use of liposomes.

Example 9

Drug Manufacturing

The membrane receptor reagent and assay disclosed here also has utility for drug manufacturing. This is particularly useful for biotherapeutic drugs. Many biotherapeutic drugs function by interacting with specific target membrane receptors. In contrast to traditional pharmaceuticals, which typically are comparatively small (low molecular weight) molecules with well-defined structures, biotherapeutics are typically larger molecules, such as proteins, which have a more complex structure that is less well defined. Due to their complex structure, protein based biotherapeutic drugs can be produced with variable levels of posttranslational modification, and in various conformations. Such posttranslational modification and conformational states can vary as a result of subtle changes in the manufacturing process.

Many of these subtle posttranslational modifications have little effect on the biotherapeutic drug's overall charge or mass, and thus are difficult to detect by many commonly used analytical methods. For example, subtle changes, such differences between glycosylation on a first amino acid residue at a first location along the protein's peptide chain, versus glycosylation on a second amino acid residue (of the same type) at a second location along the protein's peptide chain, make little or no difference to the protein's overall mass, charge, or hydrophilic/hydrophobic balance. Thus these changes can be difficult to detect by conventional capillary electrophoresis, mass spectrometry, or 2D gel electrophoresis techniques. Such changes, however, can be very important because they can affect the binding specificity of the biotherapeutic drug, causing diminished biding to the drug's intended target membrane receptor, or enhanced binding to non-target membrane receptors, resulting in unwanted side effects.

Membrane receptor assays can be constructed that are sensitive to such minor structural variations, however. For example, a membrane receptor assay may be constructed that contains both the primary target membrane receptor for a properly formed biotherapeutic drug, and various non-target membrane receptors where defective forms of the drug might bind. The output from a manufacturing process (such as a cell culture apparatus, separation apparatus, etc.) may be monitored by a multi-component membrane test apparatus (such as discussed in example 7 and FIG. 10), and deviations from ideal production quickly detected and corrected.

An additional advantage is that the methods of the present disclosure also tend to directly disclose the biological significance of such posttranslational modification differences. If, for example, a misplaced glycosylation reaction results in a decreased binding to the appropriate target membrane receptor, or increased binding to an inappropriate non-target membrane receptor, the biological significance of the change is immediately evident. By contrast, traditional analytical methods give little clue as to the biological significance of such differences.

Thus the methods of the present disclosure can be quite useful for manufacturing process control and/or quality control purposes. This can help manufacturers improve yields and reduce the chances of inadvertently releasing bad products. Additionally, these methods can help manufacturers distinguish between various different types of manufacturing processes, and help select the manufacturing process that most consistently produces the desired form of the drug product.

The methods of the present disclosure can also help a manufacturer optimize the structure of a drug for most consistent manufacturability. For example, if the membrane receptor assay detects that a particular amino acid region along a drug's polypeptide chain has a history of problematic posttranslational variation, a manufacturer may chose to optimize this amino acid region. Again using the example of variable glycosylation between a first and a second amino acid residue, the manufacturer may chose to solve the problem by changing the structure of the drug to eliminate or alter the second amino acid residue.

The invention claimed is:

1. A membrane-receptor reagent for measuring the interaction between test analytes and target membrane receptors, comprising:

a support containing an energy-emitting surface that emits energy that varies as a function of distance from said surface;

tethers covalently or non-covalently bound to said support;

reagent ligands attached to said tethers;

a fluid lipid membrane in the form of a liposome phospholipid vesicle, or lipid bilayer mounted on a second surface that projects away from said energy emitting surface, comprising target membrane receptors that bind to target analytes and reversibly bind to said reagent ligands, wherein said target membrane receptors move fluidly within said fluid lipid membrane and further comprise integral, peripheral, or transmembrane proteins labeled with a moiety that produces a detectable signal upon receiving excitation energy; and anchoring means for irreversibly binding said fluid lipid membrane to said support;

wherein binding between said target membrane receptors and target analyte either blocks or promotes binding between said reagent ligands and said target membrane receptors, causing a change in an average distance between said target membrane receptors and said energy emitting surface, resulting in a change in said detectable signal.

2. The reagent of claim 1, in which said energy emitted by said surface is selected from the group consisting of evanescent waves, surface plasmon resonance, and electron transfer, and the detectable signal is selected from the group consisting of fluorescence, luminescence, electrochemiluminescence, electron transport, and surface plasmon resonance.

3. The method of claim 1, in which said label moiety is located on an integral or peripheral membrane protein that binds to the target membrane receptor during at least one of the various target membrane receptor conformational states.

4. The reagent of claim 1, wherein said anchor means is selected from the group consisting of protein-ligand binding reagents, electrostatic interactions, hydrophobic interactions, polymeric tethers, and polymeric meshes.

5. The reagent of claim 1, wherein said target membrane receptors are membrane proteins selected from the group consisting of 7-transmembrane proteins, G-protein coupled receptors (GPCR), toll receptors, ion channels, ABC cassette pumps, hormone receptors, biological response modifier receptors, apoptosis receptors, angiogenesis receptors, neuroreceptors, histocompatibility antigens, coagulation factors, immune response antigens, and cytochrome P450 enzymes.

6. The reagent of claim 1, wherein said target membrane receptors and test analytes are selected from membrane receptors and analytes used in drug discovery, absorption distribution, metabolism, and excretion (ADME), toxicology, cellular proliferation, cellular regulation, and medical diagnostics assays.

7. The reagent of claim 1, further comprising a reference energy source, which generates a normalization signal representative of the number of said signal generating label moieties.

8. The reagent of claim 1, wherein said support is a microarray, capillary tube, fiber optic fiber, or flow cell device.

9. A method for measuring the interaction between test analytes and target membrane receptors, comprising the steps of:
   a) providing a membrane receptor reagent comprising:
      a support containing an energy-emitting surface that emits energy that varies as a function of distance from said surface;
      tethers covalently or non-covalently bound to said support;
      reagent ligands attached to said tethers;
      a fluid lipid membrane in the form of a liposome, phospholipid vesicle, or lipid bilayer mounted on a second surface that projects away from said energy emitting surface, comprising target membrane receptors that bind to target analytes and reversibly bind to said reagent ligands, wherein said target membrane receptors move fluidly within said fluid lipid membrane and further comprise integral, peripheral, or transmembrane membrane proteins labeled with a moiety that produces a detectable signal upon receiving excitation energy; and
      anchoring means for irreversibly binding said fluid lipid membrane to said support;
   b) measuring an initial detectable signal emitted from the signal generating label moieties in said reagent;
   c) adding a sample comprising target analytes to said membrane-receptor reagent, wherein binding between said target membrane receptors and target analyte either blocks or promotes binding between said reagent ligands and said target membrane receptors, causing a change in the average distance between the target membrane receptors and the energy emitting surface, resulting in a change in the detectable signal; and
   d) measuring changes in said detectable signal after sample has been added, wherein said changes in said detectable signal indicates the interaction between said target analyte and said target membrane receptors.

10. The method of claim 9, in which said label moiety is located on an integral or peripheral membrane protein that binds to the target membrane receptor during at least one of the various target membrane receptor conformational states.

11. The method of claim 9, used as a method of manufacturing a drug compound, in which said drug compound is manufactured by a manufacturing process selected from the group consisting of cell culture apparatus or separation apparatus, in which the test analytes are candidate drug molecules, and the method is used to detect amd correct deviations from ideal production.

12. The method of claim 9, wherein said energy-emitting surface emits evanescent waves, and said detectable signal is a fluorescent or luminescent signal.

13. The method of claim 9, in which the changes in the detectable signal are adjusted by a reference signal.

14. The method of claim 9, where said support is a microarray, capillary tube, fiber optic fiber, or flow cell device.

15. The method of claim 9, wherein said target membrane receptors and test analytes are selected from membrane receptors and analytes used in drug discovery, absorption distribution metabolism and excretion (ADME), toxicology, cellular proliferation, cellular regulation, and medical diagnostics assays.

16. The method of claim 9, wherein fluidic switch elements dynamically direct the passage of the test analytes to different test devices or regions of the test device.

17. A method for making a drug compound, wherein said drug compound is produced by methods selected from the group consisting of cell culture apparatus and separation apparatus, and wherein deviations from ideal production are quickly detected by the steps of:
   a) providing a membrane-receptor reagent comprisng:
      a support containing an energy-emitting surface that emits energy that varies as a function of distance from said surface;
      tethers covalently or noncovalently bound to said support;
      reagent ligands attached to said tethers;
      a fluid lipid membrane in the form of a liposome, phospholipid vesicle, or lipid bilayer mounted on a second surface that projects away from said energy emitting surface, comprising target membrane receptors that bind to target drug molecules and reversibly bind to said reagent ligands, wherein said target membrane receptors move fluidly within said fluid lipid membrane and further comprise integral, peripheral, or transmembrane membrane proteins labeled with a moiety that produces a detectable signal upon receiving excitation energy, and
      anchoring means for irreversibly binding said fluid lipid membrane to said support;
   b) measuring an initial detectable signal emitted from the signal generating label moieties in said reagent;
   c) adding a sample comprising target drug molecules output by said manufacturing process to said membrane-receptor reagent, wherein binding between said target membrane receptors and target analyte either blocks or promotes binding between said reagent ligands and target membrane receptors, causing a change in the average distance between the target membrane receptors and the energy-emitting surface, resulting in a change in the detectable signal; and d) measuring changes in said detectable signal after sample has been added, wherein said changes in said detectable signal indicates the amount of interaction between said target drug molecules and said target membrane receptors, and wherein said signal is used to correct said cell culture apparatus or said separation apparatus when said deviations from ideal production are detected.

18. The method of claim 17, in which the drug molecules are proteins, and the changes in the detectable signal represent different posttranslational modification states or different conformational states of the drug compound.

19. The method of claim 17, in which the drug molecules are proteins, and the changes in the detectable signal represent different posttranslational modification states or different conformational states of the drug compound, and the method is used for manufacturing process control or quality control purposes.

20. The method of claim 17, in which the drug molecules are manufactured by a process that produces a variable mixture of different molecular forms of the drug, and the method is used for manufacturing process control or quality control purposes.

* * * * *